United States Patent
Stoy et al.

(10) Patent No.: US 12,016,539 B2
(45) Date of Patent: *Jun. 25, 2024

(54) FLEXIBLE SURGICAL DEVICES

(71) Applicant: INTUITIVE SURGICAL OPERATIONS, INC., Sunnyvale, CA (US)

(72) Inventors: Katherine D. Stoy, Mountain View, CA (US); Samuel Kwok Wai Au, Mountain View, CA (US); Carolyn M. Fenech, San Jose, CA (US); Giuseppe Maria Prisco, Calci Pisa (IT)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/841,500

(22) Filed: Jun. 15, 2022

(65) Prior Publication Data
US 2022/0304668 A1    Sep. 29, 2022

Related U.S. Application Data

(63) Continuation of application No. 17/014,566, filed on Sep. 8, 2020, now Pat. No. 11,399,814, which is a (Continued)

(51) Int. Cl.
*A61B 17/00* (2006.01)
*A61B 34/00* (2016.01)
*A61B 34/30* (2016.01)

(52) U.S. Cl.
CPC ........ *A61B 17/00234* (2013.01); *A61B 34/30* (2016.02); *A61B 34/71* (2016.02);
(Continued)

(58) Field of Classification Search
CPC ......... A61B 34/30; A61B 34/71; A61B 34/27; A61B 2017/00309; A61B 17/00234;
(Continued)

(56) References Cited

U.S. PATENT DOCUMENTS

| | | |
|---|---|---|
| 3,946,727 A | 3/1976 | Okada et al. |
| 4,271,845 A | 6/1981 | Chikashige et al. |

(Continued)

FOREIGN PATENT DOCUMENTS

| | | |
|---|---|---|
| EP | 1836986 A2 | 9/2007 |
| WO | WO-2009117696 A1 | 9/2009 |

OTHER PUBLICATIONS

Haga, Yoichi et al., "Small diameter hydraulic active bending catheter using laser processed super elastic alloy and silicone rubber tube," 3rd IEEE/EMBS Special Topic Conference on Microtechnology in Medicine and Biology, 2005, pp. 245-248, IEEE.
(Continued)

*Primary Examiner* — Lynsey C Eiseman
*Assistant Examiner* — Daniel Tehrani
(74) *Attorney, Agent, or Firm* — Haynes & Boone, LLP.

(57) ABSTRACT

A method for operating a medical device includes measuring a configuration of a tube, receiving a desired configuration of the tube, determining an actuation input to bend the tube to the desired configuration, and transmitting the actuation input to at least one force transmission element that is actuatable to alter the tube between a flexible state and a stiffened state. Altering the tube from the flexible state to the stiffened state includes simultaneously applying first and second tension forces to first and second force transmission elements, respectively, to compress and shorten a length of the tube. The method further includes receiving a first command to place the tube in the flexible state, reducing longitudinal compression on the tube in response to the first
(Continued)

command, receiving a second command to place the tube in the stiffened state, and longitudinally compressing the tube in response to the second command.

16 Claims, 12 Drawing Sheets

Related U.S. Application Data continuation of application No. 15/824,534, filed on Nov. 28, 2017, now Pat. No. 10,813,629, which is a continuation of application No. 14/713,793, filed on May 15, 2015, now abandoned, which is a continuation of application No. 12/946,741, filed on Nov. 15, 2010, now Pat. No. 9,055,960.

(52) U.S. Cl.
CPC ........ *A61B 34/72* (2016.02); *A61B 2017/003* (2013.01); *A61B 2017/00309* (2013.01); *A61B 2017/00318* (2013.01); *A61B 2017/00336* (2013.01)

(58) Field of Classification Search
CPC .... A61B 2017/003; A61B 2017/00318; A61B 2017/00336; A61B 34/72
See application file for complete search history.

(56) References Cited

U.S. PATENT DOCUMENTS

| | | | |
|---|---|---|---|
| 4,580,551 A | 4/1986 | Siegmund et al. | |
| 4,873,965 A | 10/1989 | Danieli | |
| 5,325,845 A | 7/1994 | Adair | |
| 5,482,029 A | 1/1996 | Sekiguchi et al. | |
| 5,766,196 A | 6/1998 | Griffiths | |
| 5,807,241 A | 9/1998 | Heimberger | |
| 5,879,352 A | 3/1999 | Filoso et al. | |
| 6,749,560 B1 | 6/2004 | Konstorum et al. | |
| 6,986,771 B2 | 1/2006 | Paul et al. | |
| 7,090,683 B2 | 8/2006 | Brock et al. | |
| 7,147,650 B2 | 12/2006 | Lee | |
| 7,214,230 B2 | 5/2007 | Brock et al. | |
| 7,320,700 B2 | 1/2008 | Cooper et al. | |
| 7,678,117 B2 | 3/2010 | Hinman et al. | |
| 7,720,322 B2 | 5/2010 | Prisco et al. | |
| 7,766,821 B2 | 8/2010 | Brunnen et al. | |
| 7,867,241 B2 | 1/2011 | Brock et al. | |
| 8,142,464 B2 | 3/2012 | Mitusina | |
| 9,055,960 B2 | 6/2015 | Stoy et al. | |
| 10,813,629 B2 | 10/2020 | Stoy et al. | |
| 11,399,814 B2 | 8/2022 | Stoy et al. | |
| 2001/0021843 A1 | 9/2001 | Bosselmann et al. | |
| 2002/0177750 A1 | 11/2002 | Pilvisto et al. | |
| 2004/0059257 A1 | 3/2004 | Gaber | |
| 2004/0199052 A1 | 10/2004 | Banik et al. | |
| 2004/0225183 A1 | 11/2004 | Michlitsch et al. | |
| 2005/0131279 A1 | 6/2005 | Boulais et al. | |
| 2005/0234433 A1 | 10/2005 | Wang et al. | |
| 2006/0111615 A1 | 5/2006 | Danitz et al. | |
| 2006/0178556 A1 | 8/2006 | Hasser et al. | |
| 2007/0156019 A1* | 7/2007 | Larkin ............... A61B 34/20 600/104 |
| 2007/0221700 A1 | 9/2007 | Ortiz et al. | |
| 2007/0249896 A1 | 10/2007 | Goldfarb et al. | |
| 2007/0282358 A1 | 12/2007 | Remiszewski et al. | |
| 2008/0065102 A1 | 3/2008 | Cooper | |
| 2008/0065110 A1 | 3/2008 | Duval et al. | |
| 2008/0091170 A1 | 4/2008 | Vargas et al. | |
| 2008/0097398 A1 | 4/2008 | Mitelberg et al. | |
| 2009/0024141 A1 | 1/2009 | Stahler et al. | |
| 2009/0062602 A1 | 3/2009 | Rosenberg et al. | |
| 2009/0118712 A1 | 5/2009 | Carter et al. | |
| 2009/0137952 A1 | 5/2009 | Ramamurthy et al. | |
| 2009/0240110 A1 | 9/2009 | Miyawaki et al. | |
| 2009/0259141 A1 | 10/2009 | Ewers et al. | |
| 2009/0299343 A1 | 12/2009 | Rogers | |
| 2010/0010299 A1 | 1/2010 | Bakos et al. | |
| 2010/0030063 A1 | 2/2010 | Lee et al. | |
| 2010/0082041 A1 | 4/2010 | Prisco | |
| 2010/0160724 A1 | 6/2010 | Prisco | |
| 2010/0234831 A1 | 9/2010 | Hinman et al. | |
| 2010/0298642 A1 | 11/2010 | Trusty et al. | |
| 2010/0331820 A1 | 12/2010 | Prisco et al. | |
| 2010/0332030 A1 | 12/2010 | Larkin et al. | |
| 2011/0004157 A1 | 1/2011 | Dewaele et al. | |
| 2011/0071544 A1 | 3/2011 | Steger et al. | |
| 2011/0282491 A1 | 11/2011 | Prisco et al. | |
| 2012/0123441 A1 | 5/2012 | Au et al. | |
| 2015/0245826 A1 | 9/2015 | Stoy et al. | |
| 2020/0397423 A1 | 12/2020 | Stoy et al. | |

OTHER PUBLICATIONS

PCT/US2011/058398 International Search Report and Written Opinion of the International Searching Authority, dated Feb. 21, 2012, 10 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

FLEXIBLE SURGICAL DEVICES

CROSS-REFERENCE TO RELATED APPLICATIONS

This application is a continuation of U.S. patent application Ser. No. 17/014,566, filed Sep. 8, 2020, which is a continuation of Ser. No. 15/824,534, filed Nov. 28, 2017, now U.S. Pat. No. 10,813,629, which is a continuation of U.S. patent Application Ser. No. 14/713,793, filed May 15, 2015, which is a continuation of U.S. patent application Ser. No. 12/946,741, filed Nov. 15, 2010, now U.S. Pat. No. 9,055,960, all of which are incorporated by reference herein in their entirety.

TECHNICAL FIELD

The present teachings relate generally to flexible surgical devices. More particularly, the present teachings relate to flexible surgical devices that can be varied between flexible and stiffened states for minimally invasive surgery.

BACKGROUND

Minimally invasive surgical techniques generally attempt to perform surgical procedures while minimizing damage to healthy tissue. One particular technique for achieving this goal employs flexible surgical devices that are able to reach a target work site inside a patient by at least partially following a natural lumen, such as, for example, the digestive tract, blood-carrying lumens, or other lumens, of the patient. Following a natural lumen, for example, can allow a surgeon to operate at a work site while making fewer and/or smaller incisions through healthy tissue, although an incision may be needed at locations where the flexible device enters or leaves a natural lumen.

Surgical devices that are able to follow a natural lumen or other tortuous paths must therefore be flexible, which requires the devices to have properties and abilities that may not exist or be needed in other surgical instruments. Furthermore, although a surgical device must be flexible enough to navigate a tortuous path, in order to properly manipulate a surgical tool (e.g., an end effector) positioned at a distal end of the device, the surgical device must also provide a stable base once positioned at a work site.

In certain surgical applications and devices, however, a rigid minimally invasive instrument may be more effective for carrying out various procedures. Such instruments' inherent stiffness may be useful for tasks such as retraction, dissection, and suture tightening because a flexible device, even if prevented from bending by holding its actuating mechanisms stationary, is less stiff than a rigid instrument of similar outer diameter. As another example, if two minimally invasive instruments are used at an internal surgical work site, it is often desirable to have these instruments angled to one another so as to provide a triangulation that allows a surgeon to view the work site (e.g., using an endoscope) without the instruments blocking the view. In addition, such instrument triangulation often provides a more effective configuration for various surgical tasks (e.g., dissection, suturing, knot tying, etc.) than instruments that are oriented relatively parallel to one another.

Some conventional surgical devices that are actuatable between flexible and stiffened states have interconnected articulating links in a variety of arrangements to provide bending in one and/or multiple degrees of freedom (DOF) when in a flexible state. Such devices generally also include a force transmission mechanism (e.g., tension elements) interconnected to the links to control the bending of the device in the flexible state and to place the device in the stiffened or flexible state. Other devices may use other methods of rigidizing an instrument. For example, U.S. Patent Application Publication No. US 2009/0299343 A1 (filed May 25, 2008; entitled "Stiffening Assembly") discloses leaf structures that may be compressed to stiffen a flexible structure. As another example, U.S. Patent Application Publication No. US 2008/0091170 A1 (filed Jun. 30, 2006; entitled "Cannula System for Free Space Navigation and Method of Use") discloses stiffening embodiments that include thermal, vacuum, and pressure stiffening methods, as well as tension element rigidizing methods. Yet another example is U.S. Patent Application No. US 2010/0160724 A1 (filed Dec. 23, 2008; entitled "Flexible Surgical Instrument with Links Undergoing Solid-State Transitions"), which discloses a long link made of a shape memory alloy or another material having one state in which the link is sufficiently flexible to bend as needed to pass through a curved entry guide and another state in which the link returns to a desired shape and is sufficiently rigid for precise controlled movement. Since these structures have a relatively large number of different parts, the costs associated with manufacturing and assembling these parts can be relatively high. Thus, flexible minimally invasive surgical instruments have certain advantages over rigid straight or curved minimally invasive surgical instruments, and vice-versa. Likewise, both instrument types have certain disadvantages in both use and construction. It is desirable, therefore, to have a single minimally invasive surgical instrument that includes the benefits of both flexible and rigid instruments while at the same time minimizing their effective disadvantages.

To navigate tight, tortuous paths and perform complex motions (e.g., at a surgical work site), it may therefore be desirable to provide a surgical device that is sufficiently flexible to follow a variously curved path in a flexible state, while also providing sufficient rigidity in a stiffened state. It may also be desirable to provide a surgical device that can transition between flexible and stiffened states, using, for example, existing actuation systems and controls. Further, it may be desirable to provide a surgical device that can transition between flexible and stiffened states, can be made of relatively simple structures, can reduce the number of components and/or differently configured components, and/or can provide for relatively robust manufacturing.

SUMMARY

The present teachings may solve one or more of the above-mentioned problems and/or may demonstrate one or more of the above-mentioned desirable features. Other features and/or advantages may become apparent from the description that follows.

In accordance with various exemplary embodiments of the present teachings, a surgical device can include a tube comprising a wall having a plurality of slits oriented generally transverse to a longitudinal axis of the tube. Each of the slits may be defined by opposing surfaces. The surgical device can further include a force transmission element coupled to the tube. In a flexible state of the tube, at least some of the opposing surfaces defining respective slits are separated from one another, and in a stiffened state of the tube, a force exerted on the force transmission element causes the opposing surfaces of each slit to contact one another.

In accordance with various additional exemplary embodiments of the present teachings, a method can include longitudinally compressing a surgical instrument tube when a command to place the tube in a stiffened state is received. Longitudinally compressing the surgical instrument tube causes opposing surfaces of slits in the tube to contact one another. The method can further include reducing the longitudinal compression on the surgical instrument tube when a command to place the tube in a flexible state is received, and reducing the longitudinal compression allows the opposing surfaces of at least some of the slits to be separated from one another.

Additional objects and advantages will be set forth in part in the description which follows, and in part will be obvious from the description, or may be learned by practice of the present teachings. The objects and advantages may be realized and attained by means of the elements and combinations particularly pointed out in the appended claims and their equivalents.

It is to be understood that both the foregoing general description and the following detailed description are exemplary and explanatory only and are not restrictive of the claims.

BRIEF DESCRIPTION OF THE DRAWINGS

The present teachings can be understood from the following detailed description either alone or together with the accompanying drawings. The drawings are included to provide a further understanding of the present teachings, and are incorporated in and constitute a part of this specification. The drawings illustrate one or more embodiments of the present teachings and together with the description serve to explain certain principles and operation.

DETAILED DESCRIPTION

Figure 1:
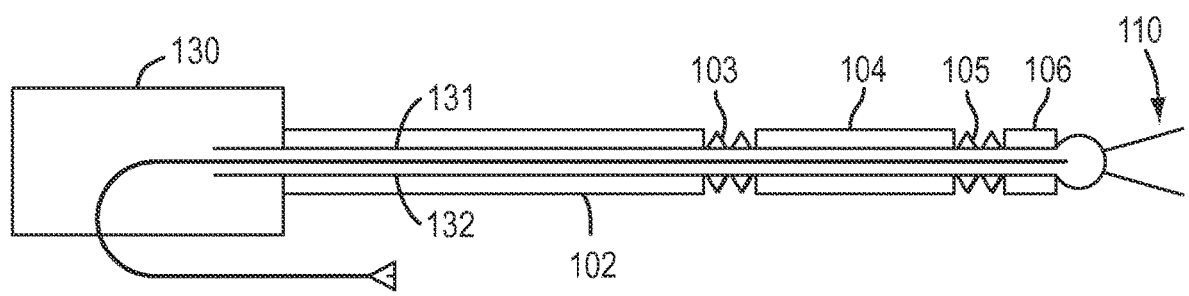
FIG. 1 is a schematic view of an exemplary embodiment of a surgical device in accordance with the prior art.

This description and the accompanying drawings that illustrate exemplary embodiments should not be taken as limiting and the claims define the scope of the present teachings. Various mechanical, compositional, structural, electrical, and operational changes may be made without departing from the scope of this description and the invention as claimed, including equivalents. In some instances, well-known structures, and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Some conventional surgical devices, including articulated arms and structures used to support and move surgical tools, are either substantially flexible or rigid, while other surgical devices are transitioned between flexible and rigid states. For minimally invasive surgery, it may be desirable for a surgical device to achieve both a flexible state and a stiffened state. Accordingly, exemplary embodiments of the present teachings consider surgical devices that can be altered between a flexible state and a stiffened state. These devices include, for example, a tube that has a plurality of slits along at least a portion of the tube, for example, slits through the tube wall.

In various exemplary embodiments, the slitted tube may be interconnected with other structures, such as, for example rigid link structures, to form the articulable surgical device. In other exemplary embodiments, the slitted tube may be used alone, for example, in place of one or more conventional articulable serial link structures. Thus, exemplary surgical devices may include, for example: (i) arms that have a series of two or more passive, flexible tubes connected by joints having at least one DOF, and (ii) active, continuously flexible tubes having at least one DOF that can be used alone to replace an articulating serial link structure (i.e., the tube itself can form the articulating arm). As those of ordinary skill in the art would understand, however, the embodiments as described generally above and in detail below are exemplary only and not intended to be limiting of the present teachings or claims. Surgical devices in accordance with the present teachings may, for example, also include hybrid structures, which include at least one passive, flexible tube portion and at least one active, continuously flexible tube portion. Moreover, flexible slitted tubes in accordance with various exemplary embodiments may be altered between passive and active states, for example, via control systems that adjust the tension in tension mechanisms associated with the tubes.

Exemplary embodiments described herein include various minimally invasive surgical devices, which may, for example, be used in conjunction with various robotic surgical systems. Robotic surgical systems are known, and examples of certain telerobotic surgical features and components may be found in systems such as the da Vinci® Surgical System (specifically, a Model IS3000, marketed as the da Vinci® Si™ HD™ Surgical System), commercialized by Intuitive Surgical, Inc. of Sunnyvale, Calif.

As used herein, the term "flexible" and variations thereof in association with a mechanical structure, such as, for example, a tube, should be broadly construed. The term describes structures (e.g., a tube) that can be repeatedly bent and restored to its original shape without permanent deformation and/or other harm to the structure. As those of ordinary skill in the art would understand, many "rigid" structures have a slight inherent resilient "bendiness" due to material properties, although such structures are not considered "flexible" as the term is used herein. As those of ordinary skill in the art would further understand, a structure's flexibility may also be expressed in terms of its stiffness. Those ordinarily skilled in the art would appreciate that devices having a flexible state and a stiffened state are in differing relative states of flexibility (or rigidity). For example, the flexible state may provide a degree of bending to the device that is significantly greater than when the device is in the stiffened state, in which the device acts more like a single, rigid structure.

In accordance with the present teachings, a tube may also be either actively or passively flexible. An actively flexible tube may be bent by using forces originating from sources associated with the tube itself, such forces acting on the tube to intentionally bend it (e.g., in an amount and direction) as desired. For example, one or more force transmission elements may be routed lengthwise along the tube and offset from the tube's center longitudinal axis, so that a force on one or more of the force transmission elements acts on the tube to cause the tube to bend. Exemplary force transmission elements that can be utilized to bend an actively flexible tube can include but are not limited to, for example, tension elements that transmit a force on the tube when a tension force is exerted on the elements (e.g., cables, filaments, wires, rods, etc.) and/or compression elements that transmit a force on the tube when a compressive force is exerted on the elements (e.g., rods). In either case, the force transmission elements should also be sufficiently flexible in order to be able to bend as the tube bends, but still enable a force to be transmitted to the tube to bend and/or stiffen the tube. A passively flexible tube is bent by a force external to the tube and its associated components. For example, during a minimally invasive procedure, an external force may be the reactive force the tube experiences when pushed against tissue. As those of ordinary skill in the art would understand, however, an actively flexible tube, when not actuated by its associated sources of force, may be passively flexible. Furthermore, a tube may include one or more actively and passively flexible portions in series.

As used herein, the term "a flexible state" refers to a state in which the tube's flexible nature is being used. In other words, when "in the flexible state" a tube is either actively or passively bendable or bent. For example, tension in one or more tension elements may cause the tube to bend (i.e., while tension on the remaining tension elements is relaxed), or a force external to the tube may cause the tube to bend when tension on one or more tension elements is relaxed (i.e., when tension on all the tension elements is relaxed).

As used herein, the term "a stiffened state" refers to a state in which the tube is actively rigidized. In other words, when "in the stiffened state" a tube is effectively rigid so as to be substantially prevented from passive bending of the tube. For example, a force may be exerted to substantially uniformly compress the tube along its longitudinal axis to thereby stiffen the tube (i.e., to provide sufficient rigidity for a stable base). In exemplary embodiments, the compression force on the tube may be exerted by applying equal tension on one or more tension elements associated with the tube. Thus, in the stiffened state, the tube is stiff enough so that it can be effectively controlled as a single, rigid piece.

FIG. 1 schematically illustrates a side elevation view of an exemplary surgical device 100. Surgical device 100 includes, for example, a serial link structure (i.e., an arm) comprising a series of segments 102, 104, and 106 interconnected by joints 103 and 105. As depicted, a surgical end effector 110 (e.g., grasper, needle driver, shears, cautery tool, camera, and/or the like) is coupled to the distal end of segment 106. As illustrated and described in greater detail below, the surgical device 100 may be actuated via cables 131 and 132 by an actuation mechanism 130. In one exemplary embodiment, the segments 102, 104, and 106 can be rigid links.

Figure 2:
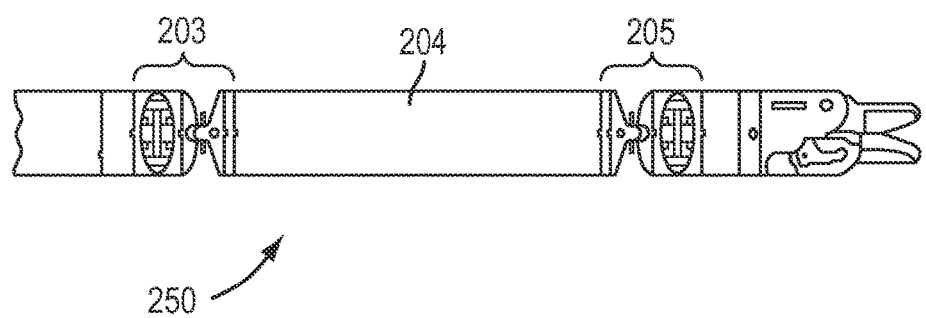
FIG. 2 is a side elevation view of one exemplary embodiment of the distal portion of a surgical device in accordance with the prior art.

Although various structures can be used to form the surgical device 100. FIG. 2 shows a side elevation view of one exemplary embodiment of the mechanical distal portion 250 of a surgical device, such as disclosed, for example, in U.S. Application Publication No. US 2008/0065102 A1 (filed Jun. 13, 2007; entitled "Surgical Instrument with Parallel Motion Mechanism"), the entire contents of which are incorporated by reference herein. As shown in FIG. 2, the surgical device distal portion 250 can include illustrative joints 203 and 205 that each has two hinges pivotable around orthogonal axes. The joints 203 and 205 are interconnected by a rigid link 204, which can be in the form of a rigid tube. Thus, by providing differing pivoting arrangements in joints 203 and 205, various shapes can be achieved over the distal portion 250 of the surgical device to achieve one or more of pitch and yaw movement of the arm to perform complex motions that can be desirable for various surgical tasks, examples of which include but are not limited to knot tying, resection, suturing, etc. Permitting such complex motions can also be useful in traversing tortuous paths and accurately reaching a target site in a patient's body. Reference is made to U.S. Application Publication No. US 2008/0065102 for various arrangements to achieve various bending patterns in the arm.

Those of ordinary skill in the art would understand, however, that surgical device distal portion 250 is exemplary only and illustrates one exemplary configuration for the surgical device 100 that is represented schematically in FIG. 1. The arrangement of elements shown in FIGS. 1 and 2 is not intended to be limiting of the present teachings and claims, but rather, as explained in more detail below, depict exemplary surgical devices with which embodiments in accordance with the present teachings can be utilized. Surgical device 100 may therefore comprise various types, numbers, and/or configurations of components (e.g., interconnected joints, links, etc.) depending upon the particular surgical application desired. In various embodiments, for example, joints 103 and 105 may function as a multi-link section (e.g., as independently controlled joints), whereas in various additional embodiments joints 103 and 105 may function as a pivoting joint pair (e.g., as mechanically coupled joints). Reference is also made to U.S. patent application Ser. No. 12/945,734 (filed Nov. 12, 2010; entitled "Tension Control in Actuation of Multi-Joint Medical Instruments", and U.S. patent application Ser. No. 12/618,608, (filed Nov. 13, 2009; entitled "Curved Cannula Instrument"), the entire contents of both of which are incorporated by reference herein, for various types and configurations of devices suitable for application of the flexible tubes of the present teachings.

Passively Flexible Surgical Devices

In accordance with aspects of the present teachings, a passively flexible, stiffenable tube is made by placing a large number of relatively thin slits in the tube wall across a width of the tube. These slits allow the tube to be flexible, and accordingly the widths of the various slits in the tube wall increase or decrease as the tube bends. To place the tube in a stiffened state, the tube is longitudinally compressed, which closes the slits so that opposing surfaces of each slit are pressed against each other. In this stiffened state, the tube effectively functions as an uncut (e.g., solid wall) tube. When the longitudinal compression is relaxed (e.g., reduced or removed), the tube returns to a flexible state, in which the opposing surfaces of each slit are spaced apart from each other. These aspects are discussed in further detail below.

Figure 3:
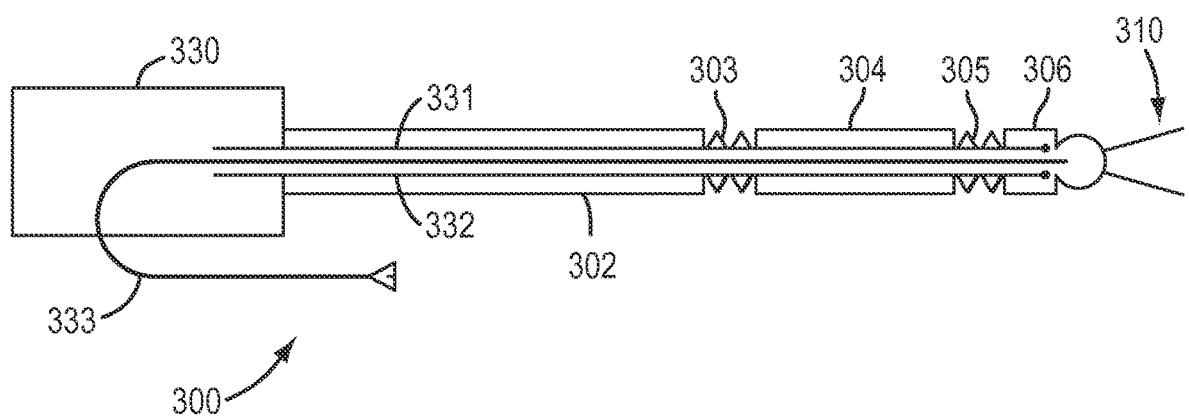
FIG. 3 is a schematic view of an exemplary embodiment of a surgical device in accordance with the present teachings.
Figure 3A:
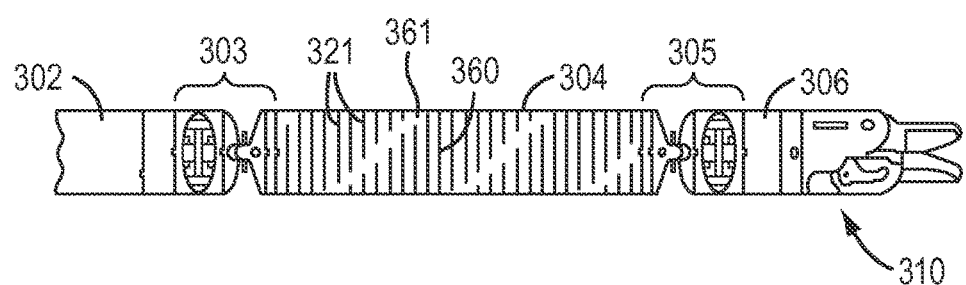
FIG. 3A is a side elevation view of a distal portion of FIG. 3.
Figure 3B:
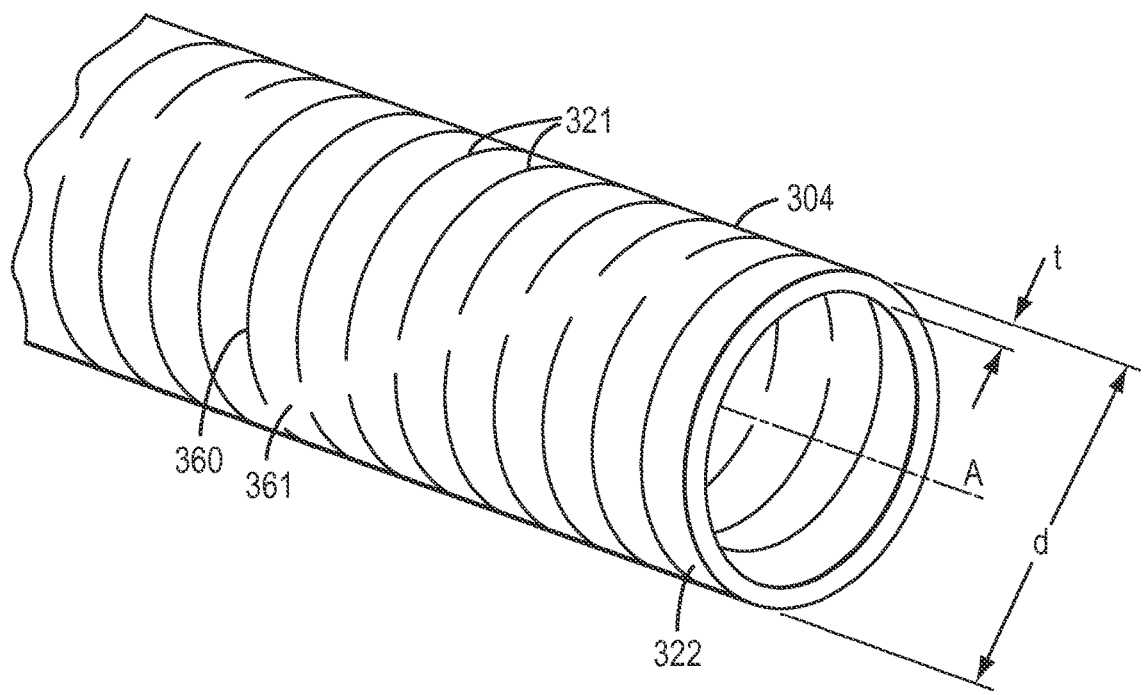
FIG. 3B is a partial perspective view of the tube of FIG. 3.

Referring now to FIG. 3, in accordance with various exemplary embodiments of the present teachings, a surgical device 300 can comprise at least one passive, flexible segment, such as a passive, flexible tube 304 having a plurality of slits 321 in the tube wall, as shown in more detail in FIGS. 3A and 3B. Surgical device 300 includes, for example, a serial link structure (i.e., an arm) comprising a series of segments 302, 304, and 306 interconnected by joint pairs 303 and 305. In various exemplary embodiments, a surgical end effector 310 (e.g., grasper, needle driver, shears, cautery tool, camera, and the like) is coupled to the distal end of segment 306. By way of example, therefore, the rigid link 204 in the embodiment of FIG. 2 can be replaced with the passive, flexible tube 304 to provide an arrangement that can offer various desirable features, as described further below.

As used herein the term "tube" refers to structures that are generally hollow and can pass and/or contain material. Tubes may have variously shaped cross-sections (e.g., circular, oval, elliptical, polygonal, etc., or combinations thereof), and in some instances a tube may have one or more openings in its sidewall. In various embodiments, a tube may also be filled with a material that provides low resistance to bending (e.g., a flexible material such as a soft plastic, metallic braid, spring, etc.). As shown in FIG. 3B, in an exemplary embodiment, the passive, flexible tube 304 is an elongate, hollow structure having a longitudinal axis A and a diameter d. In various embodiments, as illustrated in FIGS. 3 and 3A, the tube 304 is at least a portion (e.g., a segment) of a surgical device 300 designed to be inserted into a patient to perform minimally invasive surgery. Accordingly, in various embodiments, with reference to FIG. 3B, the tube 304 has an outer diameter d, ranging from about 2 mm to about 12 mm, such as, for example, from about 2 mm to about 8 mm, or, for example, from about 2 mm to about 5 mm. The thickness t of the tube wall 322, in various embodiments, ranges from about 0.07 mm to about 0.38 mm, for example, from about 0.12 mm to about 0.25 mm for a tube having an outer diameter of about 5 mm. Furthermore, in various embodiments wherein the tube 304 is a segment of a serial link structure (i.e., comprising only a portion of the arm), the tube 304 has a length ranging from about 6 mm to about 80 mm.

Those of ordinary skill in the art would understand, however, that the tube 304 may have various dimensions (e.g., diameters and/or lengths) and be formed from various resilient and biocompatible materials including, for example, stainless steel, titanium, shape-memory alloys (e.g., various pseudoelastic/superelastic materials, such as nitinol), plastic or a composite, and that the dimensions and material used for the tube 304 may be chosen as desired based on surgical application, strength, cost, and other such factors.

As illustrated in FIGS. 3A and 3B, the slits 321 in the wall 322 of the tube 304 are disposed along at least a portion of the length of the tube 304, and are oriented generally transverse to the longitudinal axis A of the tube 304. In other words, each slit 321 lies within a plane that is generally transverse to the longitudinal axis A of the tube 304. Those of ordinary skill in the art would understand, however, that the slits 321 may have various orientations with respect to the longitudinal axis A of the tube 304. In various embodiments, for example, each of the slits 321 may be oriented in planes angled from about 45 degrees to about 90 degrees (i.e., perpendicular) relative to the longitudinal axis A of the tube 304. In an exemplary embodiment, the slits 321 are formed by laser cutting, and they extend through the thickness t of the tube wall 322. Depending on the material of tube 304, however, the slits 321 may be formed using various techniques and/or methods as would be understood by those of ordinary skill in the art, including, for example, using a slitting saw, water jet cutting, injection molding, and/or electric discharge machining (EDM). Furthermore, in various embodiments (not shown), the slits 321 may extend partially through the thickness of the tube wall 322 (e.g., formed in an outer surface of the tube wall).

The tube 304 may comprise various slit configurations (e.g., patterns, numbers, arrangement relative to each other, and/or dimensions). Those of ordinary skill in the art would understand, for example, that the mechanical properties of the tube 304 can be modified by changing the configuration. Consequently, depending on a particular surgical application, those of ordinary skill in the art would understand how to determine suitable slit patterns, numbers, arrangements, and dimensions, including, for example, slit width (as measured by the distance between opposing tube wall surfaces that define a slit), slit density (the number of slits 321 per unit length of tube 304), and the length of each slit 321 (the distance between two ends of a slit 321 measured around a periphery of the tube 304), to achieve desired tube properties (e.g., flexibility and stiffness). In various exemplary embodiments, for example, a tube 304 with an outer diameter of about 5 mm may have a slit width in the range of about 0.001 inches to about 0.010 inches, with spacing between each slit in the range of about 0.005 inches to about 0.030 inches. Furthermore, by way of example, although FIG. 3A shows the tube 304 having slits 321 along substantially the entire length of the tube 304, the slits 321 could be formed only along a portion of the tube or could be formed in discrete sections along the length of the tube 304.

In various exemplary embodiments of the present teachings, the slits 321 may be configured to provide various ranges of bending about the longitudinal axis A of the tube 304 when the tube 304 is in the flexible state. In various embodiments, for example, the slits 321 provide a range of bending ranging from about 10 degrees to about 45 degrees. In various additional embodiments, the slits 321 provide a range of bending of about 10 degrees per inch of length of the tube 304. Differing patterns and arrangements of the slits 321 may also be used in differing regions along the length of the tube 304 to provide varying ranges of bending or stiffness along a length of tube 304. In various embodiments, for example, the slits 321 may be configured to provide less flexibility at the ends of the tube 304 (i.e., at locations where the passive, flexible tube 304 connects to joints 303 and 305) as compared to central regions along the length of the tube 304 where greater flexibility may be desired.

As shown in FIGS. 3A and 3B, to provide a substantially isotropic bend in the tube 304, in various embodiments, the slits 321 may follow a helical path around the periphery of the tube 304 (e.g., the slits 321 may comprise a helical pattern). In other words, the slits 321 are cut along a line 360 that spirals around the tube 304. In one exemplary embodiment, for example, the slits 321 are cut at a relatively fine pitch of about 0.5 mm (turns per longitudinal length of tube 304). In such a configuration, each cut along the line is about 170 degrees of the tube circumference, followed by a non-cut length of about 30 degrees of the tube circumference. This cut pattern, for example, provides 40 degrees of offset between the start point of each slit 321 (i.e., between slit ends that are stacked adjacent one another as the pattern moves longitudinally along the tube 304). As illustrated in FIGS. 3A and 3B, this cut pattern results in a double helix pattern of slits 321 and a double helix pattern of uncut lengths (e.g., solid, uncut wall regions between slit ends) along the length of the tube 304. As shown with particular reference to FIG. 3A, the line 361 depicted by the uncut regions illustrates one of the double helixes that spirals around the tube 304 (although at a relatively coarser pitch than the line 360 along which the cuts are made). Although not wishing to be bound by a particular theory, it appears that this spiral formed by line 361 of uncut regions acts as a coil spring would act to support and stiffen the slitted tube 304. Thus, as would be understood by those of ordinary skill in the art, various tube characteristics (e.g., longitudinal stiffness, plasticity, etc.) may be determined by the parameters of the spiral of uncut regions 361 (e.g., the pitch of the line 360 along which the cuts are made, the cut lengths along the line 360, and the uncut lengths along the line 361).

It can be seen that for certain slit patterns, the tube ends may rotate with reference to one another as the tube is longitudinally compressed to place it in the stiffened state. And so, in various embodiments, for example, to prevent twisting of the ends of the tube 304 relative to each other during compression of the tube 304 (i.e., during the stiffened state), the slits 321 on a first length of the tube 304 may follow a right-hand helical path and the slits 321 on a second length of the tube 304 may follow a left-hand helical path (not shown). Alternatively, the slits may be patterned so that a known rotation of one end of the tube with reference to the opposite end is obtained when the tube is compressed into the stiffened state.

To alter the tube 304 between a flexible state (see FIG. 5A) and a stiffened state (see FIGS. 5C and 5D), one or more force transmission elements can be coupled to the tube 304. As would be understood by those of ordinary skill in the art, a force transmission element may comprise a variety of tension elements, such as, for example, a cable, a wire, a filament, or a rod, and/or compression elements, such as, for example, a push rod. Suitable materials for the force transmission elements can include metals and polymers, for example. As would be further understood by those of ordinary skill in the art, force transmission elements may have various configurations (e.g., numbers and/or locations), and the number and location of used may be chosen as desired based on surgical application, efficiency, cost, and other such factors. The force transmission elements, whether tension or compression elements, have sufficient strength to transmit a force to the tube to stiffen and/or bend the tube as desired, but also are sufficiently flexible to permit bending of the force transmission element with the bending of the tube. The force transmission elements may be part of an actuation/tensioning system commonly used in various articulating minimally invasive surgical devices (e.g., arms, wrists, guide tubes). For example, the one or more force transmission elements can be part of the actuation mechanism 330 used to control the overall surgical device 300 in the exemplary embodiment of FIG. 3.

Figure 4:
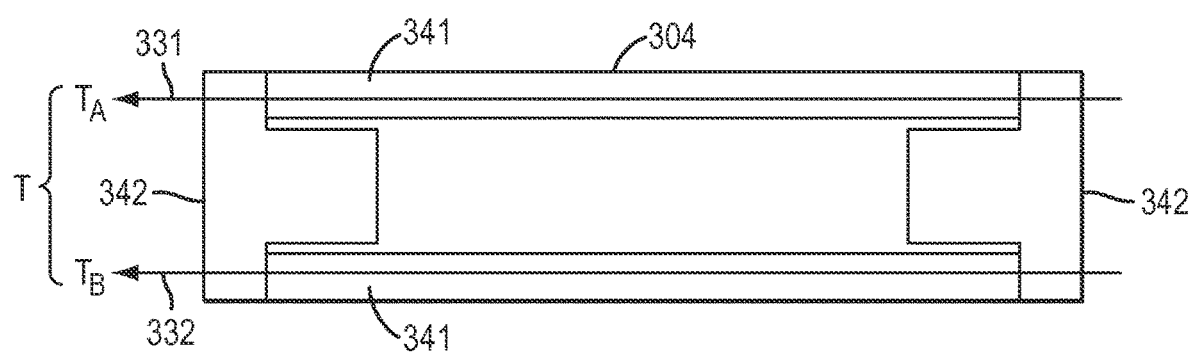
FIG. 4 is a schematic view of the tube of FIG. 3 illustrating tension elements in accordance with the present teachings.

As shown in FIGS. 3 and 4, for example, in various embodiments, the force transmission elements may comprise tension elements in the form of a plurality of cables (two of which cables 331 and 332 are depicted in the view of FIGS. 3 and 4, however those having ordinary skill in the art would understand that any number of cables may be used depending on the desired application and movement of the surgical device) positioned within the tube 304. As shown in FIG. 3 and mentioned above, in various embodiments, the cables 331 and 332 may comprise actuation cables that are connected to and used to control (e.g., articulate and/or rigidize) segments of the serial link structure that are distal to the passive flexible tube 304 (e.g., joint 305 and/or end effector 310) in the exemplary embodiment of FIGS. 3 and 3A.

As illustrated in the cut away view of FIG. 4 showing the interior of the tube, in various embodiments, cables 331 and 332 can be muted internally through the lumen of the tube 304 to ultimately connect to an actuation mechanism at a proximal end of the surgical device and to one or more segments of the surgical device distal to the tube 304, as shown by the extension of the cables 331 and 332 past the tube on the right hand side in the view of FIG. 4. In exemplary embodiments, it may be desirable, though not necessary, to include routing members 341, shown schematically, to receive and position the cables 331 and 332 proximate an interior of the tube wall. Exemplary routing members are discussed in more detail below with reference to the exemplary embodiment of FIG. 11. Routing members 340 can be used to keep the cables 331 and 332 away from the center of the lumen of the tube 304 so as to reduce the risk of the cables 331 and 332 interfering with other components (e.g., fiber sensors, actuation members for controlling the end effector, and/or other instruments) that may be present in the lumen of the tube 304.

FIG. 4 also depicts exemplary end caps 342 that may be optionally provided on the ends of the tube 304 to use as a coupling structure to connect the tube to other tubes or structures in a serial link structure. Although not shown in FIG. 4, the end caps 342 may be provided with exterior surface features or other structures that can provide a coupling to another structure in the serial link structure.

Figure 5A:
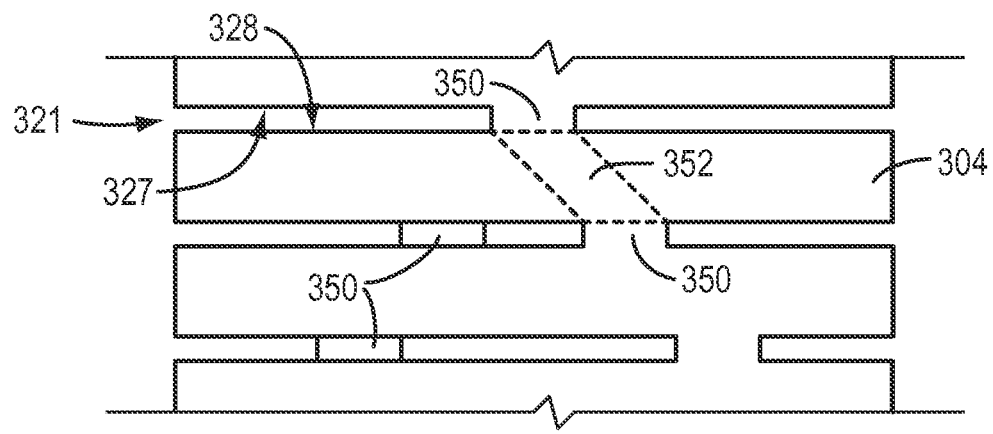
FIG. 5A is a diagrammatic view of the tube of FIG. 3 in a flexible state.
Figure 5B:
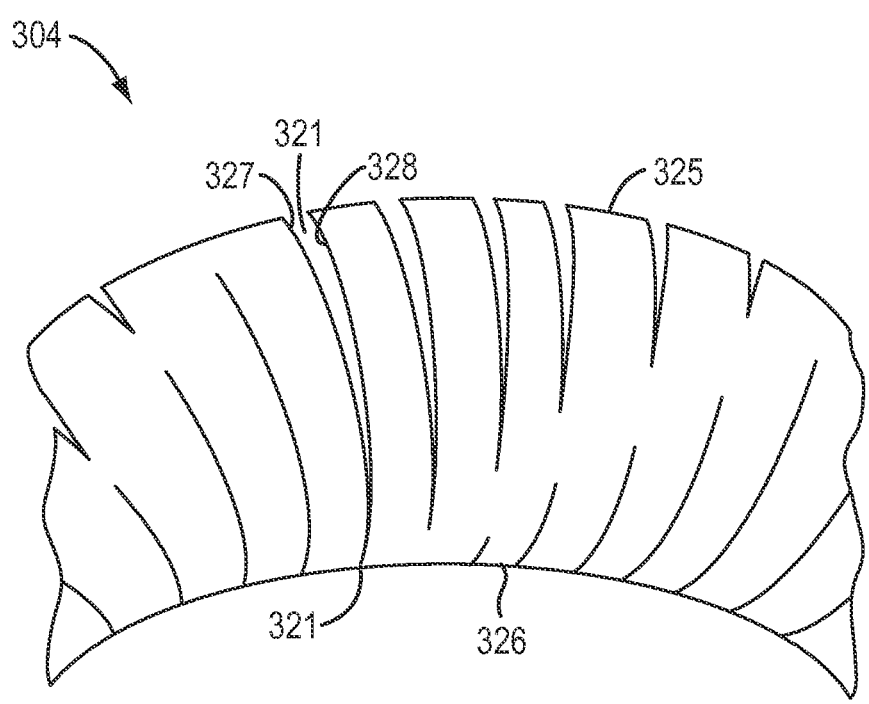
FIG. 5B is a partial perspective view of the tube of FIG. 3 in a flexed (bent) state.

The passive, flexible tube 304 is placed in the flexible state by relaxing cables 331 and 332. The tube 304 may be placed in the flexible state, for example, to navigate through a natural lumen to reach a work site. As shown in FIG. 5B, in the flexible state, the tube 304 may passively bend upon external forces acting thereon, such as, for example, when the surgical device 300 encounters a wall of the lumen during its navigation therethrough. In this manner, tissue damage may be minimized by allowing the tube 304, as well as potentially other articulable portions of the device 300, to passively bend upon a portion of the surgical device 300 impacting the lumen. As would be understood by those of ordinary skill in the art, in various embodiments wherein the cables 331 and 332 comprise actuation cables (e.g., to actively control joint 305 and/or end effector 310), the passive, flexible tube 304 may also passively bend via the movement of the other surgical components of device 300.

The pattern of slits 321 on the tube 304 may be thought of as creating a web structure that when uncompressed allows the structure to bend into the spaces within the web and when compressed prevents the structure from bending by closing the spaces within the web. FIG. 5A illustrates, for example, a diagrammatic view of the tube 304 in a flexible state. As shown in FIG. 5A, the slits 321 are open, so that opposing surfaces 327 and 328 defining a respective slit are apart. At the end of each slit 321 is a web connecting element 350 (i.e., an uncut region of the tube wall). As also illustrated in FIG. 5A (as well as in FIGS. 3A, 3B, 5B, 5C, and 10), the web connecting elements 350 are progressively offset from one another by a small amount along the length of the tube 304 so that they are arranged in a helical pattern in the tube 304. Thus, regions 352, as shown by the dashed line parallelogram shape, exist in the tube 304 between the web connecting elements 350. Although not wishing to be bound by a particular theory, it appears that, as the tube 304 bends, slight deformations occur in the web connecting elements 350 (e.g., due to twisting of the connecting element).

Accordingly, as would be understood by those of ordinary skill in the art, upon application of a bending moment (e.g., via an external force), the passive, flexible tube 304 may bend. In other words, as illustrated in FIG. 5B, at least some of the slits 321 on an outer bend radius 325 of the tube 304 may open such that opposing slit surfaces 327 and 328 are spaced apart from each other, while at least some of the slits 321 on an inner bend radius 326 of the tube 304 constrict such that the opposing surfaces 327 and 328 defining those slits 321 are in contact with, and in some cases pressed against, each other.

Figure 5C:
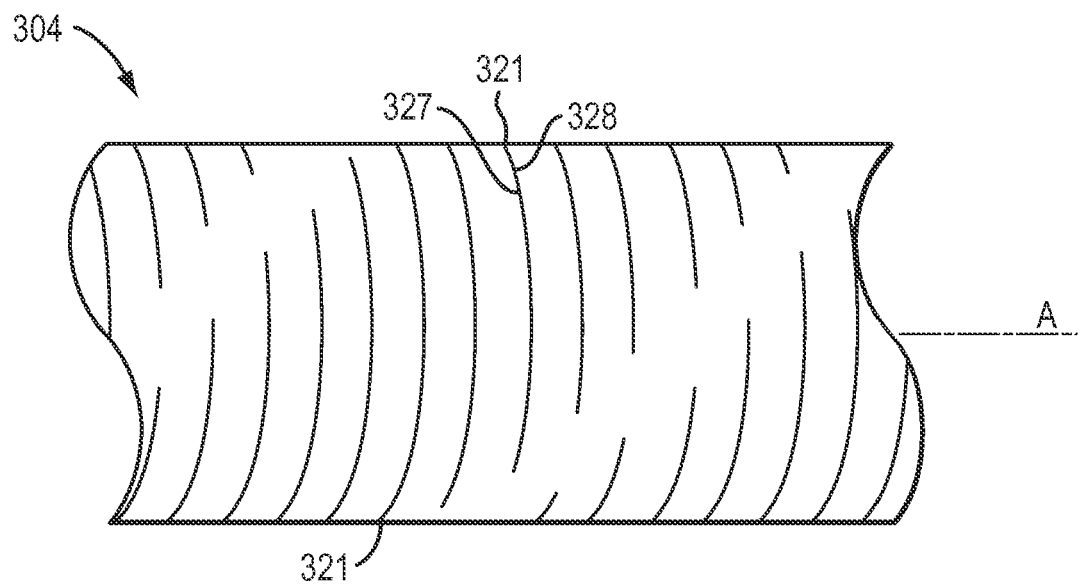
FIG. 5C is a partial perspective view of the tube of FIG. 3 in a stiffened state.
Figure 5D:
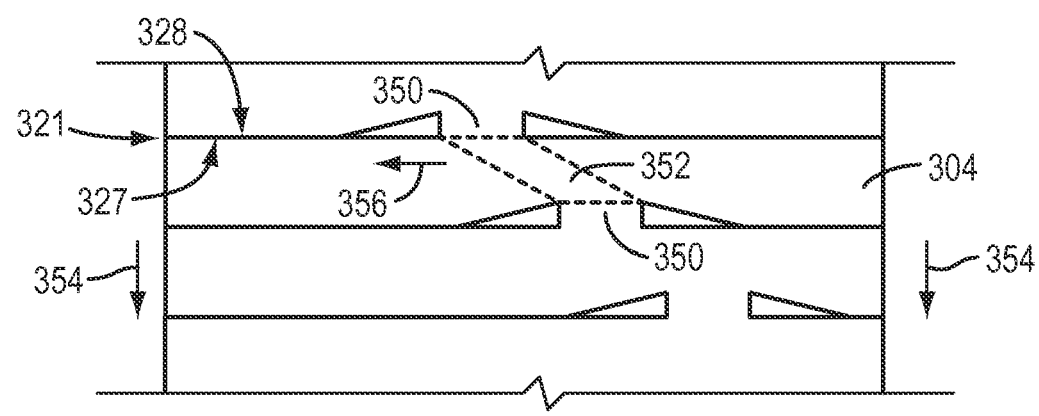
FIG. 5D is a diagrammatic view of the tube of FIG. 3 in a stiffened state.

The passive, flexible tube 304 can be placed in the stiffened state by applying tension T (see FIG. 4) to cables 331 and 332 (i.e., wherein both T.sub.A and T.sub.B have the same tension T), which may be desirable, for example, once the end effector 310 is located at a work site. As shown in FIGS. 5C and 5D, in the stiffened state, the tube 304 is straightened and compressed along the longitudinal axis A. The stiffened state of the tube 304 can provide a stable base for operation of the end effector 310 by preventing or substantially minimizing bending of the tube 304. As depicted in FIG. 5C, in the stiffened state, the tube 304 is compressed along the longitudinal axis to constrict the slits 321 so that opposing slit surfaces 327 and 328 contact each other, and, for example, press against each other.

FIG. 5D illustrates a diagrammatic view of the tube 304 in a stiffened state. As shown in FIG. 5D, the tube 304 has been longitudinally compressed, as illustrated by arrows 354 (force transmission elements, such as internal cables 331 and 332, are not shown). This longitudinal compression brings opposing slit surfaces 327 and 328 against one another so that the slit is effectively closed. It can be seen that some longitudinal shortening of tube 304 occurs as the slits 321 are closed. As described above, for the configuration shown, the web of slits also tends to rotate (twist) around the tube's longitudinal axis during compression. Although not wishing to be bound by any particular theory, it appears that this rotation is caused by a small deformation in the regions 352, which results in the next distal-most web connecting element 350 being further offset from each preceding web connecting element 350, as illustrated by arrow 356 in FIG. 5D.

Those of ordinary skill in the art will understand, however, that various patterns of slits 321, and hence various patterns of web connecting elements 350 (i.e., uncut regions of the tube wall), may be used to provide various tube 304 bending and rigidizing features. For example, as described above, a helical pattern of connecting elements, at a particular slit density, may produce a known compression twist along a particular tube length. Accordingly, two substantially equal length portions of the tube 304, with opposite helical patterns of connecting elements 350, will produce opposite twists that will effectively offset one another so that there is no recognizable twist between opposite ends of the tube 304.

Figure 5E:
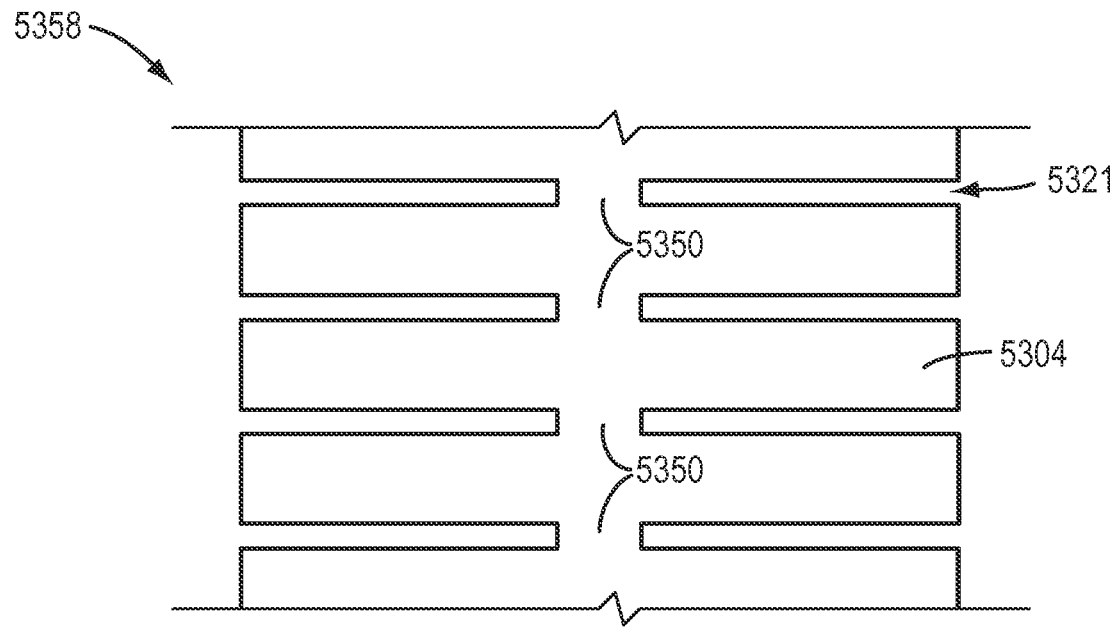
FIG. 5E illustrates a partial diagrammatic view of a tube in accordance with various additional embodiments of the present teachings.
Figure 5F:
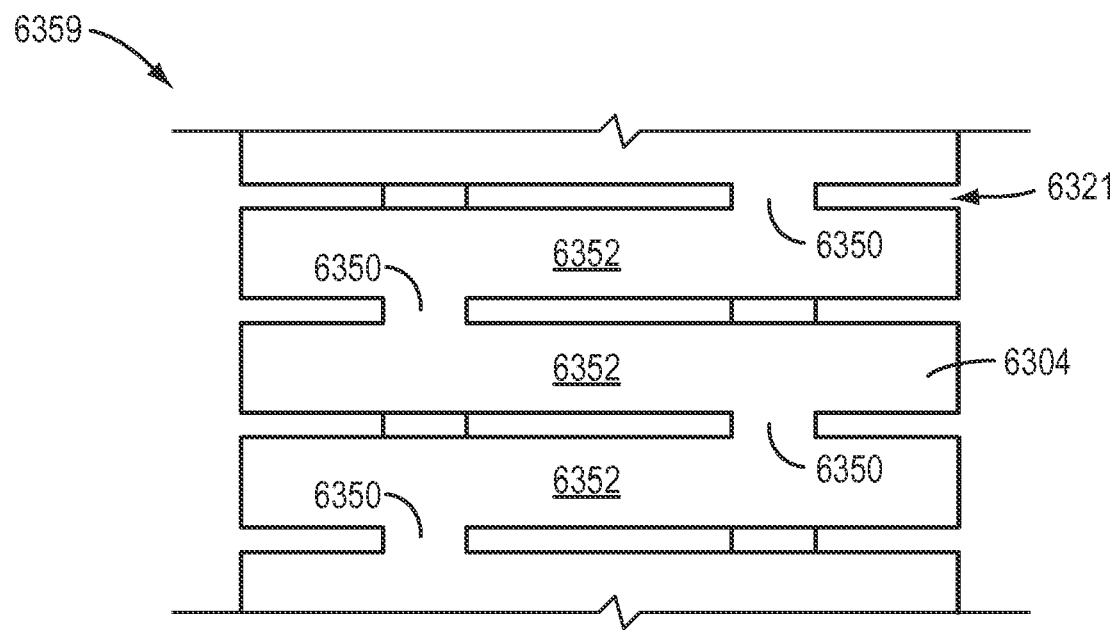
FIG. 5F illustrates another partial diagrammatic view of a tube in accordance with various additional embodiments of the present teachings.

FIGS. 5E and 5F, for example, illustrate diagrammatic views of a tube showing slit/connecting element patterns in accordance with various additional embodiments of the present teachings. As shown in pattern 5358 of FIG. 5E, the connecting elements 5350 are longitudinally aligned. Accordingly, as would be understood by those of ordinary skill in the art, pattern 5358 induces a preferential bending in tube 5304, so that tube 5304 bends to the left and to the right, but not into or out of the plane of the paper (opposite side connecting elements are hidden behind the ones shown). Further, maintaining a relatively small width of connecting elements 5350 relative to the diameter of the tube 5304 can facilitate the ability to place the tube 5304 in a stiffened state. As shown in pattern 6359 of FIG. 5F, each subsequent pair of connecting elements 6350 are offset from the preceding pair of connecting elements 6350 by 90 degrees. Accordingly, as would be understood by those of ordinary skill in the art, pattern 6359 induces no preferential bending direction for the tube 6304, and there is effectively no longitudinal twist when tube 6304 is compressed and stiffened. Furthermore, in this embodiment, since the areas 6352 between the connecting elements 6350 are relatively large, material stress within areas 6352 appears to be minimized during compression. As mentioned above, those of ordinary skill in the art will also understand that various other patterns of slits and connecting elements may be used with various slit densities and/or tube lengths to produce desired tube flexibility and stiffening features.

Although it is envisioned that a variety of cable actuation methods and techniques known to those skilled in the art may be implemented to alter the tube 304 between a flexible and stiffened state, various exemplary embodiments in accordance with the present teachings may utilize actuation methods and techniques such as disclosed, for example, in U.S. patent application Ser. No. 12/945,734 (filed Nov. 12, 2010; entitled "Tension Control in Actuation of Multi-Joint Medical Instruments"), U.S. patent application Ser. No. 12/494,797 (filed Jun. 30, 2009; entitled "Compliant Surgical Device"), and U.S. Patent Application Publication No. US 2010/0082041 A1 (filed Sep. 30, 2008; entitled "Passive Preload and Capstan Drive for Surgical Instruments"), the entire contents of each of which are incorporated by reference herein.

Figure 6:
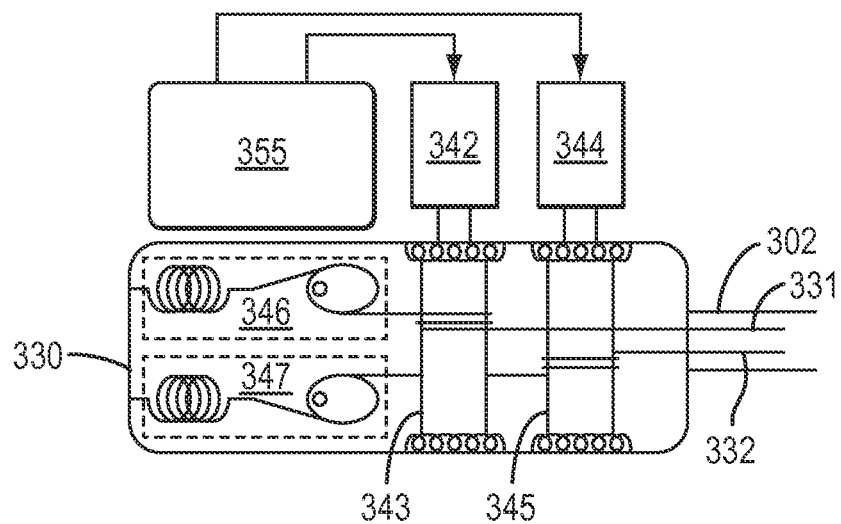
FIG. 6 is a schematic view of an actuation mechanism in accordance with the present teachings.

As shown in the schematic representation of FIG. 3, for example, in various embodiments, a surgical device 300 may further comprise an actuation mechanism 330 to actuate the one or more force transmission elements, thereby altering the passive, flexible tube 304 between flexible and stiffened states. The actuation mechanism 330 is, for example, a transmission mechanism that receives forces from an actuator and transmits the forces to the device's distal components. As illustrated in the schematic representation of FIG. 6, in various exemplary embodiments, the actuation mechanism 330 acts as a transmission that converts torques applied by drive motors (i.e., actuators) 342 and 344 into tensions in respective cables 331 and 332. As shown in FIG. 6, in various embodiments, the actuator comprises one or more motors 342 and 344 that directly couple to capstans 343 and 345 around which respective cables 331 and 332 wrap. The cables 331 and 332 can therefore be actuated by respective motors 342 and 344 to compress the tube 304 (e.g., to put the tube in a stiffened state). In various additional embodiments, the actuator is backdrivable to overcome a base pretension force in the cables 331 and 332. In other words, a baseline tension force in the cables 331 and 332, applied by respective passive preload systems 346 and 347, may be sufficient to compress the tube 304 (e.g., to put the tube in a stiffened state), and the cables 331 and 332 can be actuated by backdriving the motors 343 and 344 to relax the cables 331 and 332, thereby placing the tube 304 in a flexible state. Reference is made to U.S. Application Publication No. US 2010/0082041 A1 for various devices and methods for actuating the cables. Briefly, the tensioning element is a tendon. The surgical device uses a passive preload system attached to the tendon, which is wrapped around a capstan. The passive preload system controls relaxed state tension in the tendon. The passive preload system can employ a spring or other structure to apply tension to the tendon. The capstan can be driven by a motor when the tendon is needed to pull on a structural member of the instrument (e.g., one or more of the instrument's distal end components). For example, for an application of clamping pressure or movement of the structural member against resistance, capstan friction on the tendon can produce tendon tension that is many times the tension applied by the passive preload system. However, when the tendon is not needed to apply force to the member, the capstan can be freed, so that the preload system provides enough tension to prevent tendon derailment or other malfunctions. The low, preload tension in relaxed state tendons can reduce overall tendon friction, particularly in instruments with flexible shafts that actuate only some tendons for desired control inputs (e.g., distal end steering).

Although it is envisioned that a variety of control systems and methods known to those of ordinary skill in the art may be implemented to actuate the one or more force transmission elements (e.g., to alter the tube 304 between flexible and stiffened states), various exemplary embodiments in accordance with the present teachings may utilize systems and methods such as disclosed, for example, in U.S. patent application Ser. No. 12/780,417 (filed May 14, 2010; entitled "Drive Force Control in Medical Instruments Providing Position Measurements"), the entire contents of which are incorporated by reference herein. As shown in FIG. 6, for example, in various embodiments, a surgical device 300 may further comprise a control system 355 to actuate cables 331 and 332. It should be further understood that a powered actuation system is not necessarily required, and that in certain instances the necessary actuation force may be, for example, a hand-operated lever, which functions as the actuator for a force transmission element.

In various additional embodiments, a surgical device may implement sensing technology such as disclosed, for example, in U.S. patent application Ser. No. 12/490,487 (filed Jun. 24, 2009; entitled "Arm with a Combined Shape and Force Sensor") and U.S. Pat. No. 7,720,322 B2 (filed Jun. 30, 2008; entitled "Fiber Optic Shape Sensor"), the entire contents of which are incorporated by reference herein, to measure the configuration of the tube. Accordingly, to control actuation of the at least one force transmission element, various exemplary embodiments of the present teachings, may comprise a sensor configured to measure the position and/or orientation of the tip (i.e., distal end) of the tube 304 relative to the base (i.e., proximal end) of the tube 304 and a control system that receives position and/or orientation information from the sensor.

As used herein, "configuration of a tube" or "configuration of a segment" refers to a general configuration of the tube or segment that occurs from having one or more bends in the tube or segment of a tube. For example, the configuration can refer to a measured position and/or orientation of the tip (i.e., distal end) of the tube or segment relative to the position and/or orientation of the base (i.e., proximal end) of the tube or segment. Those of ordinary skill in the art would therefore understand that as used herein, the term configuration can refer to one or more parameters that can be determined (e.g., measured) based on the three-dimensional geometric shape of the tube or segment; such parameters can include, but are not limited to, for example, position, orientation, velocity, acceleration etc.

As shown schematically, for example, in FIG. 3, a sensor, such as, for example, an optical fiber 333 is routed through the instrument 300 so that the distal end of fiber 333 terminates, for example, at or near the distal end of segment 306. The position and orientation of the distal end of instrument 300 can be determined, for example, by a segment of the fiber 333 within segment 306. In various embodiments, actuation of the cables 331 and 332 may therefore be robotically controlled or computer-assisted using an existing control system and sensor 333 implementing a feedback loop that monitors, for example, joint pairs 303, 305, and segment 306. As those of ordinary skill in the art would understand, such a control scheme gives joints 303 and 305 an "active stiffness" dependent on the system's characteristics (e.g., actuation cable stiffness, lever arm, etc.) and control parameters (e.g., gains, etc.). Accordingly, as long as the tube 304 is stiffer than the feedback controlled joints 303 and 305 (i.e., in the stiffened state), impact on an existing control system is minimal.

As above, those ordinarily skilled in the art would understand that surgical device 300 is exemplary only and not intended to be limiting of the present teachings and claims, but rather to illustrate one exemplary configuration of a surgical device which may utilize the passive, flexible tubes in accordance with exemplary embodiments of the present teachings. A surgical device may therefore comprise various types, numbers, and/or configurations of components depending upon the particular surgical application desired.

Figure 7:
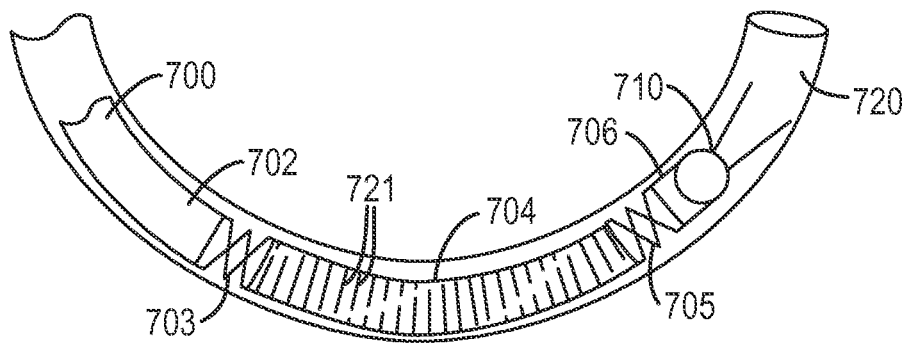
FIG. 7 is a partial side elevation view of an exemplary embodiment of a surgical system in accordance with the present teachings.
Figure 8:
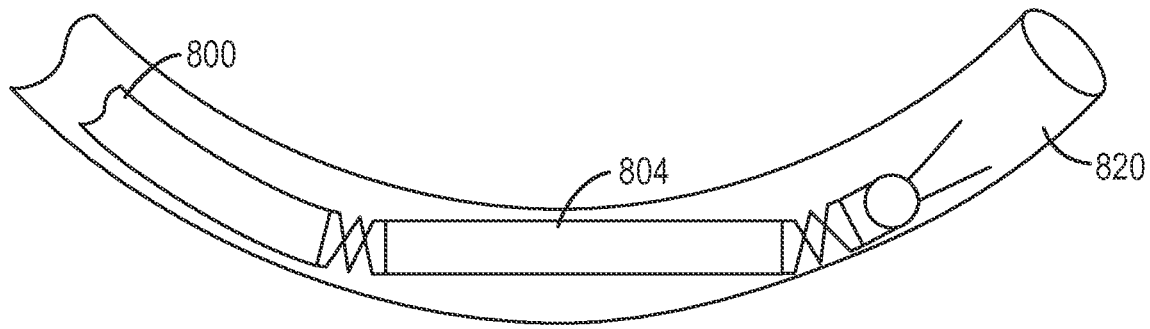
FIG. 8 is a partial side elevation view of an exemplary embodiment of a surgical system.

In accordance with various additional exemplary embodiments of the present teachings, for example, as shown in FIG. 7, a surgical system may comprise a curved cannula 720 and a surgical device 700 with a passively flexible shaft that extends through the cannula 720. The surgical device 700 may comprise several passive, flexible segments, such as a passive, flexible tube 702 (e.g., which may be made of a relatively flexible material) and a passive, flexible tube 704 having a plurality of slits 721 on an exterior surface thereof. Surgical device 700 includes, for example, a serial link structure comprising a series of segments 702, 704, and 706 interconnected by joints 703 and 705. In various embodiments, a surgical end effector 710 (e.g., grasper, needle driver, shears, cautery tool, camera, and the like) is coupled to the distal end of segment 706. By way of example, therefore, a rigid link 804 of a surgical device 800, as depicted in the embodiment of FIG. 8, can be replaced with the passive, flexible tube 704 to provide an arrangement that can offer increased flexibility to a shaft as it extends through a cannula. As would be understood by those of ordinary skill in the art, such an application allows the surgical device 700 to extend through a rigid, curved cannula 720 having a relatively small inner diameter and small bend radius (as compared with surgical device 800, which may only navigate through rigid, curved cannula 820 having a relatively large inner diameter (i.e., relative to the outer diameter of the device 800) and/or large bend radius (see FIG. 8)). Thus, when a surgical device like surgical device 700 is used, the rigid, curved cannula (or other entry guide) diameter may be made relatively smaller to minimize patient trauma. Reference is made to U.S. patent application Ser. No. 12/618,608 for various types and configurations of cannula systems suitable for application of the flexible tubes of the present teachings.

Actively Controlled, Flexible Surgical Devices

In accordance with further aspects of the present teachings, one or more slitted tubes, or segments of a slitted tube, may be actively controlled to bend in various ways. Thus, the slitted tube may be placed into a stiffened state and into a passively flexible state, as described above, and still further into an actively controlled state in which the tube is controlled to achieve a desired shape.

As discussed above, to provide flexibility to a linked surgical device, a passive, flexible tube comprising slits may be used as a segment between the device's articulated joints. To provide a stable base (e.g., for operation of a surgical end effector of the surgical device), the passive slitted tube may be compressed to straighten and stiffen the tube, for example, along with other segments (e.g., links) to which the tube is interconnected. In various other exemplary embodiments, however, rather than being used with a plurality of interconnected articulated joints (i.e., as a segment of an overall serial link structure), one or more tubes comprising a plurality of slits may be used alone to provide an active, continuously flexible, articulating arm that can replace a serial link structure (e.g., replace the link structure of FIG. 1). As with the passive tube embodiment, such an active, continuously flexible tube may be compressed to straighten and stiffen the tube by pressing the slits' surfaces against each other, thereby creating a rigid arm when desired.

Figure 9:
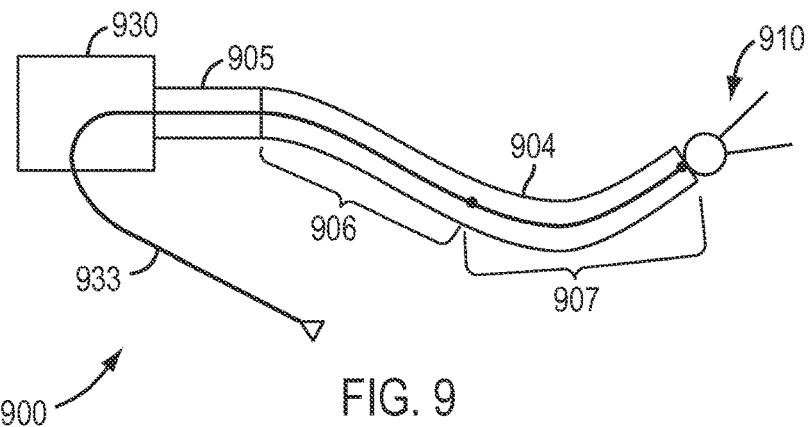
FIG. 9 is a schematic view of another surgical device in accordance with the present teachings.

FIG. 9, for example, illustrates a continuously flexible surgical device 900 wherein a slitted tube 904 makes up the entire actively controlled portion of the device 900 (i.e., there are no other serial link structures used to provide the articulation to the device 900). As illustrated, surgical device 900 includes an active, flexible tube 904 having two active, continuously flexible articulating segments 906 and 907 (e.g., a plurality of actively controlled articulating sections of one continuously flexible tube 904). As shown in FIG. 9, in various embodiments, a surgical end effector 910 (e.g., grasper, needle driver, shears, cautery tool, camera, and/or the like) is coupled to the distal end of tube 904, and the proximal end of the tube 904 is connected to a base tubular structure 905 to support the tube 904 and ultimately provide a connection to an actuation mechanism 930. Although the base structure 905 can exhibit some flexibility (e.g., be made of a somewhat flexible material), it is sufficiently rigid so as to passively bend minimally in response to movement of the segments 906, 907. Further base structure 905 can be made of a material, or otherwise reinforced (e.g., via sheaths as is described in further detail below), so that it is substantially incompressible and able to withstand a compressive force exerted by stiffening and/or bending of segments 906 or 907.

Those of ordinary skill in the art would understand that the active, flexible tube 904 may have various dimensions (e.g., diameters, wall thicknesses, and/or lengths) and be formed from various resilient materials including, for example, stainless steel, titanium, nitinol, plastic, or a composite, and that the dimensions and material used for the tube 904 may be chosen as desired based on surgical application, strength, cost, and other such factors. In various embodiments, as illustrated in FIG. 9, the active, flexible tube 904 comprises the entire arm of the surgical device 900. Accordingly, in various embodiments, each segment 906 and 907 of the tube 904 has a length ranging from about 3 to about 20 or more times the outer diameter of the tube 904. In various embodiments, each segment 906 and 907 has a different length. In various embodiments, for example, segment 906 is a relatively longer segment and segment 907 is a relatively shorter segment.

Figure 10:
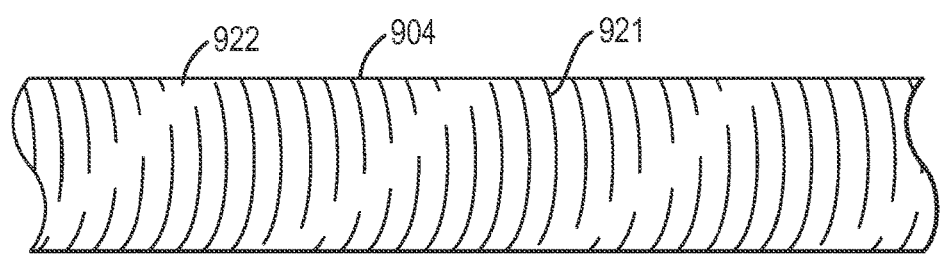
FIG. 10 is a partial elevation view of the tube of FIG. 9.
Figure 11:
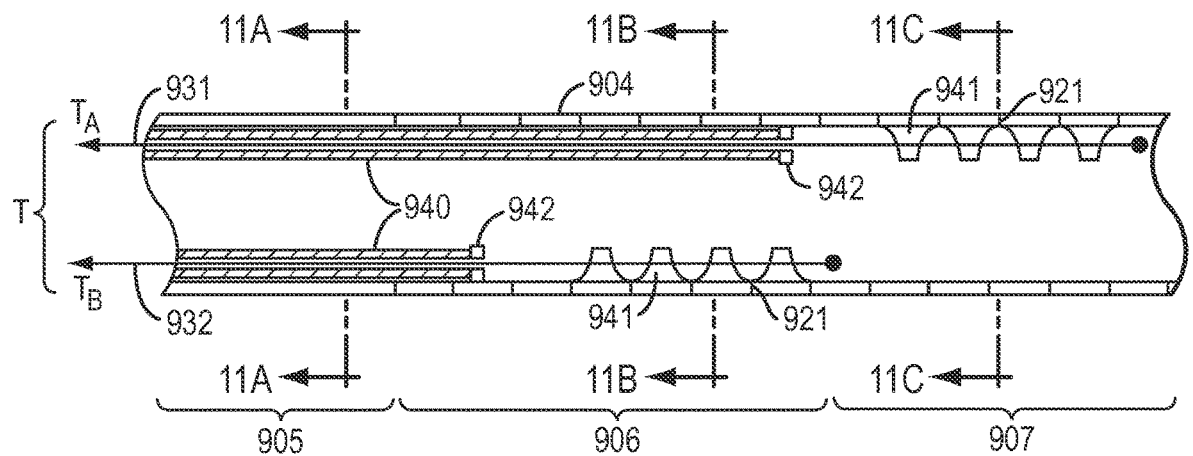
FIG. 11 is a partial cross-sectional schematic view of the tube of FIG. 9 illustrating tension elements in accordance with the present teachings.
Figure 11A:
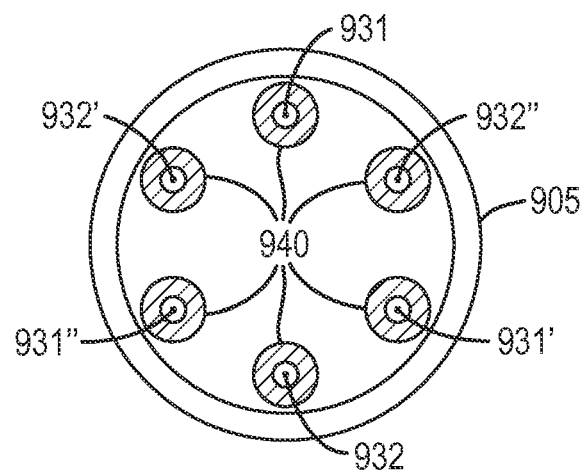
FIGS. 11A-11C are the respective cross-sectional views taken from 11A-11A, 11B-11B, and 11C-11C of FIG. 11.
Figure 11B:
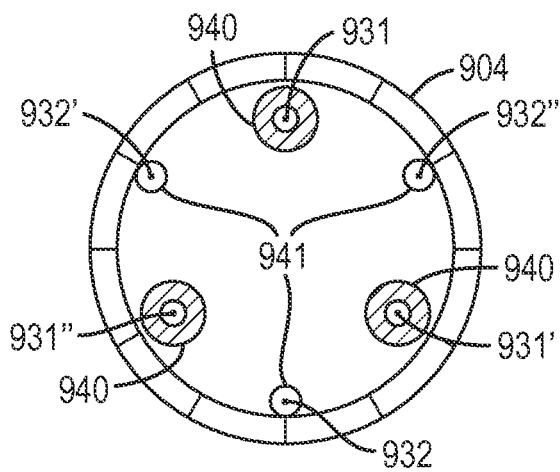
Figure 11C:
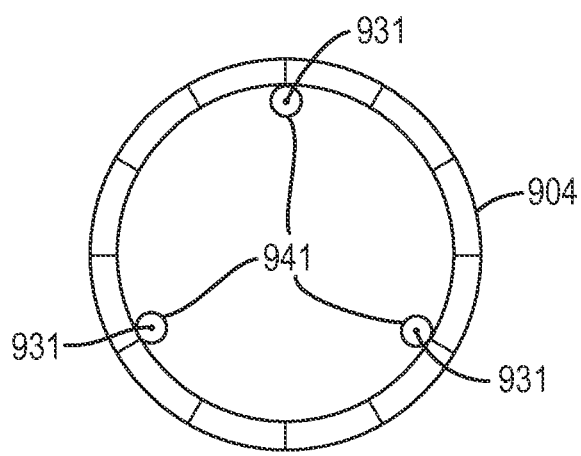

As shown in FIG. 10, and described in detail above with regard to FIGS. 3A, 3B, and 5A-5E, the active flexible tube 904 has a plurality of slits 921 in the tube wall 922. To alter the tube 904 between a flexible state (e.g., similar to that shown in FIGS. 5A and 5B) and a stiffened state (e.g., similar to that shown in FIGS. 5C and 5D), one or more force transmission elements can be coupled to the tube 904. As shown in the cross-sectional view of FIG. 11, for example, in various embodiments, the force transmission elements can comprise a plurality of tension elements, such as, for example, cables positioned within the tube 904. In the view of FIG. 11, two cables 931 and 932 are depicted as respectively corresponding to actively control the segments 907 and 906 of the tube 904. Those having ordinary skill in the art will appreciate that more than one cable may be associated with one or more of the segments to achieve multiple DOF movement of the segment. For example, as shown in the cross-sectional views of the segments 906 and 907 in FIGS. 11B and 11C, respectively, in an exemplary embodiment each of the segments 906 and 907 has three cables (931, 931', 931" corresponding to segment 907; 932, 932', and 932" corresponding to segment 906) associated therewith to actively control the motion (e.g., bending/stiffening) of the segments 906 and 907. Those ordinarily skilled in the art would appreciate that the differing segments also may have a differing number of cables (e.g., ranging from one to more than one, for example, from 1 to 4) associated therewith depending on the overall movement of the tube 904 that may be desired.

As illustrated in FIGS. 11 and 11A-11C, in various embodiments, cables 931 and 932 are routed along an interior wall of the tube 904 via routing members 941. To maintain sufficient flexibility of the tube 904 in the regions where routing members 941 are positioned to permit stiffening and/or bending of the tube 904, the routing members 941 can be configured to permit both flexing and compressing of the tube 904. Suitable routing member structures may therefore include, but are not limited to, a plurality of discrete rings, loops, hooks or other similar structures, a laser cut hypotube (for example, cut to form a plurality of rings disposed along the interior wall of the tube 904, as shown in FIG. 11), a coil spring attached at various points along its length to the interior wall, or other similar structures that permit bending and compression of the tube 904. The routing members may be attached to the interior wall of the tube via welding, or other suitable bonding or securing mechanism. In the exemplary embodiment wherein the routing members comprise a laser cut hypotube, each of the plurality of slits 921 can also extend through the hypotube. In other words, in various embodiments, the tube wall 922 with attached hypotubes 941 is laser cut in a desired pattern so that the tube/hypotube assembly substantially becomes a single, flexible piece. In various additional embodiments (not shown), one or more slitted hypotubes can be attached to an exterior surface of the tube 904 (i.e., along the exterior of the tube wall 922).

The routing members 941 may be formed from various materials including, for example, stainless steel, nitinol, titanium, reinforced plastics, and/or composite materials. Those of ordinary skill in the art would understand how to select a material for the routing members 941 based on factors such as, for example, application, flexibility, cost, etc. For routing members comprising hypotubes, suitable materials may include, for example, compressible plastics, such as, for example, expanded polytetrafluoroethylene (PTFE). In one exemplary embodiment, routing members comprising discrete rings, loops, hooks and the like may be made of wire or other filament structures that provide sufficient strength to route the cables, but also allow the tube 904 to bend and compress.

In some exemplary embodiments, it also may be desirable to incorporate structures with the flexible tube that decouple the behavior (e.g., motion and/or stiffening) of a proximal segment and a distal segment. In this way, when an articulable distal segment is bent and/or stiffened by a force transmission element that also passes through one or more proximal segments, the resulting force that is transmitted to a proximal segment can be reduced. Likewise, structures that decouple the motion between proximal and distal segments can also reduce unintended motion of distal segments based on motion of one or more proximal segments. In the exemplary embodiment illustrated in FIGS. 11 and 11A-11C, the tube 904 includes flexible, substantially incompressible sheaths 940 that extend along an interior wall of the base structure 905 and segment 906 of the tube 904. Cables that actively control a segment (e.g., 906 and/or 907) can be routed through the sheaths 940. Thus, for example, the cables 931 that are actuated to actively bend or stiffen segment 907 are routed through sheaths 940 in base structure 905 and in segment 906, and the cables 932 that are actuated to actively control segment 906 are routed through sheaths 940 in base structure 905. The sheaths 940 are separated from the interior wall of the tube 904 and tubular base structure 905, and are attached (e.g., welded, bonded, or otherwise secured) thereto at their distal ends via end caps 942. Consequently, the sheaths 940 can carry the compressive load that is exerted by actuation of the cables 931, 932 to control (e.g., bend or stiffen) a more distal flexible segment. By routing the cables 931 and 932 through the substantially incompressible sheaths 940, the actuation of the cables 931 and 932 will not transmit substantial force to the base structure 905 and the segment 906 of tube 904 to which the sheaths 940 are attached, as the sheaths 940 will tend to carry that force instead. This can avoid, for example, undesirable stiffening of the segment 906 due to the compressive loading from the actuation of cables 931 and 932.

In various exemplary embodiments, the sheaths 940 can comprise a coil tube, a partially laser cut hypotube (e.g., sufficient to provide flexibility in bending yet remain substantially incompressible), a helical hollow strand bundle of relatively stiff wire, a plastic tube, and other structures that are flexible but sufficiently incompressible so as to achieve decoupling of the transmission of the force from force transmission elements, such as, for example, cables 931 and 932, routed therethrough. As shown in FIG. 11, routing members 941 may be disposed to receive the cables 931 and 932 once they emerge from the sheaths 940 into segments that are actively controlled by the respective cables.

In use, the active, flexible tube 904 is placed in the flexible, bending state by actively applying a tension (e.g., indicated as $T_A$ and $T_B$ in FIG. 11) to selected cables 931, 931', 931", 932, 932', and/or 932" (e.g., as the surgical device 900 is navigated through a natural lumen). As illustrated in FIG. 11, applying a tension $T_A$ on cable 931 will cause segment 907 to bend in a counterclockwise direction (as viewed), while applying a tension $T_B$ on cable 932 will cause segment 906 to bend in a clockwise direction (as viewed). As would be understood by those of ordinary skill in the art, upon application of a bending moment (e.g., via an internal cable such as 931, 931', 931", 932, 932', and/or 932"), the tube 904 will bend until it reaches a stop. In other words, as illustrated in FIG. 5B with regard to slits 321, at least some of the slits 921 on an outer bend radius of the tube 904 may open such that opposing surfaces defining a respective slit are spaced apart from each other. In various embodiments, for example, upon maximum bending of the tube 904, the slits 921 on an outer bend radius of the tube 904 may open such that opposing surfaces defining a respective slit are spaced apart from each other about twice as much as when the tube 904 is in a relaxed (i.e., unbent or passively flexible) state. In this manner, the tube 904 may bend until the slits 921 on an inner bend radius of the tube 904 are fully constricted such that the opposing surfaces defining those slits 921 are in contact with, and in some cases pressed against, each other.

Figure 14A:
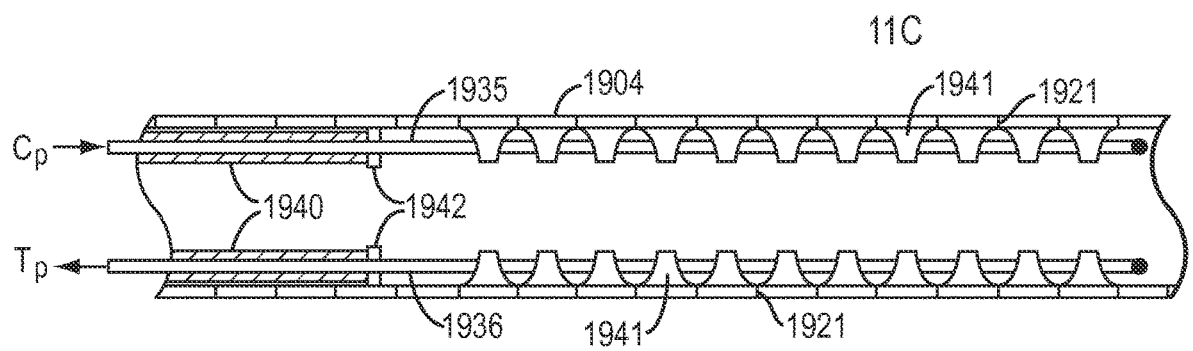
FIG. 14A is a partial cross-sectional view of yet another exemplary embodiment of a tube illustrating compression elements in accordance with the present teachings.
Figure 14B:
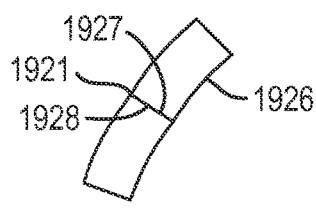
FIGS. 14B and 14C show schematic views of opposing surfaces of a slit on an inner bend radius of the tube of FIG. 14A in response to various bending forces applied to the tube.
Figure 14C:
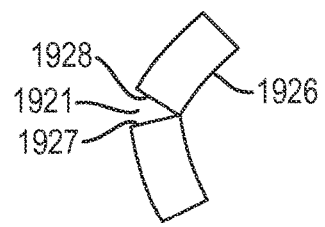

As would be understood by those of ordinary skill in the art, in various additional embodiments, to further bend the tube 904 after it reaches a stop at which the opposing surfaces defining the slits contact each other, an additional active force may be applied to the tube using a compression member that can apply a force sufficient to further expand and space apart the opposing surfaces of the slits on the outer bend radius of the tube, while causing the opposing surfaces of the slits on the inner bend radius of the tube to pivot about each other at an inner most contact edge. FIG. 14A shows a cross-sectional view of an exemplary embodiment of an active flexible tube 1904 or segment thereof that includes flexible rods 1935 and 1936 (e.g., which can act as push rods or pull rods as described below) for controlling the bending of the tube 1904. As with the tension elements described above, the rods 1935 and 1936 can be first received through sheaths 1940 and then through routing members 1941, such as the various sheaths and routing members that have been described herein. To bend the tube 1904 in a clockwise direction (as viewed), a tension force T.sub.P can be applied to the rod 1936, which can cause the tube 1904 to bend until the opposing surfaces defining the slits 1921 on the inner bend radius of the tube 1904 press against each other (e.g., as described with reference to FIG. 5B). To further bend the tube 1904 past the stop limit associated with pulling the rod 1936, a compressive force C.sub.P can be applied to the push rod 1935 along the outer bend radius of the tube 1904. This may further bend the tube 1904 such that the spacing between the opposing surfaces of the slits 1921 on an outer bend radius of the tube gets larger than the spacing that occurs as a result of pulling on rod 1936 alone (e.g., larger than that in FIG. 5B). In addition, the further bending also can result in the opposing surfaces of the slits 1921 on an inner bend radius 1926 of the tube pivoting relative to each other about an innermost contact edge. For example, as depicted in the schematic representations of FIGS. 14B and 14C of a slit 1921 on an inner bend radius I of the tube 1904, the opposing surfaces 1927, 1928 defining the slit 1921 are in contact with each other as a result of actuation of the tension element 1930, as shown in FIG. 14B. Further bending of the tube via a compression element (e.g., pushing on rod 1935) causes the opposing surfaces 1927, 1928 of the slit 1921 to pivot about an innermost contact edge upon actuation of the push rod 1935, as depicted in the schematic representation of FIG. 14C, thereby creating an opening between the opposing surfaces 1927, 1928 on the inner bend radius 1926 at least along an interior of the wall of the tube.

In various exemplary embodiments, the rods 1935, 1936, or other compression elements, are sufficiently rigid to withstand a compressive force that can be transmitted to the flexible, tube, yet sufficiently flexible to permit bending of the compression element with the bending of the tube. Also, although the exemplary embodiment of FIG. 14A illustrates compression elements (rods 1935, 1936) disposed along an interior of the tube 904, one or more compression elements could be disposed along an exterior of the tube. Further compression elements and tension elements may be used in combination in various exemplary embodiments to control the bending/stiffening of the tube.

With reference again to FIG. 11, the active, flexible tube 904 is placed in the stiffened state by applying tension T (i.e., wherein T.sub.A and T.sub.B have the same tension T) to all of the actuation cables 931, 931', 931", 932, 932', 932" (e.g., once the end effector 910 is located at a work site). As above, in the stiffened state, the tube 904 is compressed along the longitudinal axis to constrict the slits 921 so that opposing slit surfaces contact each other, and, for example, press against each other (e.g., in a manner similar to that shown in FIGS. 5C and 5D). Accordingly, the stiffened state of the tube 904 can provide a stable base for operation of the end effector 910 by preventing or substantially minimizing bending of the tube 904.

As shown in the schematic representation of FIG. 9, in various embodiments, a surgical device may further comprise an actuation mechanism 930 to actuate the one or more force transmission elements (e.g., cables in the embodiment of FIGS. 9 and 11), thereby altering the active, flexible tube 904 between flexible and stiffened states. In various exemplary embodiments, the actuation mechanism 930 acts as a transmission that converts torques applied by drive motors (i.e., actuators) into forces in respective cables such as cables 931, 931', 931", 932, 932', and 932". In various embodiments, for example, the actuation mechanism 930 can be the same as the actuation mechanism 330 described above for FIG. 6. Accordingly, details of the actuation mechanism 930 are not reiterated here. In various additional embodiments, the surgical device 900 may include a sensor, such as, for example, an optical fiber 933. As shown in FIG. 9, fiber 933 may be routed through the instrument 900 so that fiber 933's distal end terminates, for example, at or near the distal end of the tube 904. Accordingly, the configuration of each segment 906 and 907 can be determined, for example, by sensing the relative position and/or orientation of a tip portion (i.e., distal end) relative to a base portion (i.e., proximal end) of a fiber segment within each segment 906 and 907. Those of ordinary skill in the art would understand, however, that surgical device 900 is exemplary only and not intended to limit the present teachings and claims. Accordingly, aspects of the present teachings can be embodied in various surgical devices and/or instruments, such as, for example, cannula systems and guide tubes for other surgical instruments, as well as for tissue manipulating instruments themselves. Furthermore, in various embodiments, tube 904 may comprise various types (i.e., passive and active), numbers, and/or configurations of continuously flexible bending segments like 906 and 907 depending on the surgical application employed. For example, in various embodiments, segments 906 and 907 are each actively flexed by one or more (e.g., three in the exemplary embodiment described above) cables respectively. In another exemplary embodiment, the flexible tube could have three separately controlled segments with the most proximal and distal segments being active, flexible segments via one or more force transmission elements (e.g., three cables each to provide three DOF movement), and a middle segment being a passive, flexible segment. In an exemplary embodiment, the passively flexible segment may include a single, tension element along a centerline thereof to place it in a stiffened state if desired. The preceding descriptions of the numbers and types of segments of a slitted flexible tube are exemplary only and not intended to limit the scope of the present teachings or claims' various additional embodiments are contemplated and those having ordinary skill in the art would understand how to make modifications based on the teachings herein in order to provide a surgical device suitable to a desired application. Moreover, as those of ordinary skill in the art would understand, an actively flexible segment, when not actuated by its associated sources of force, can be passively flexible.

Figure 12:
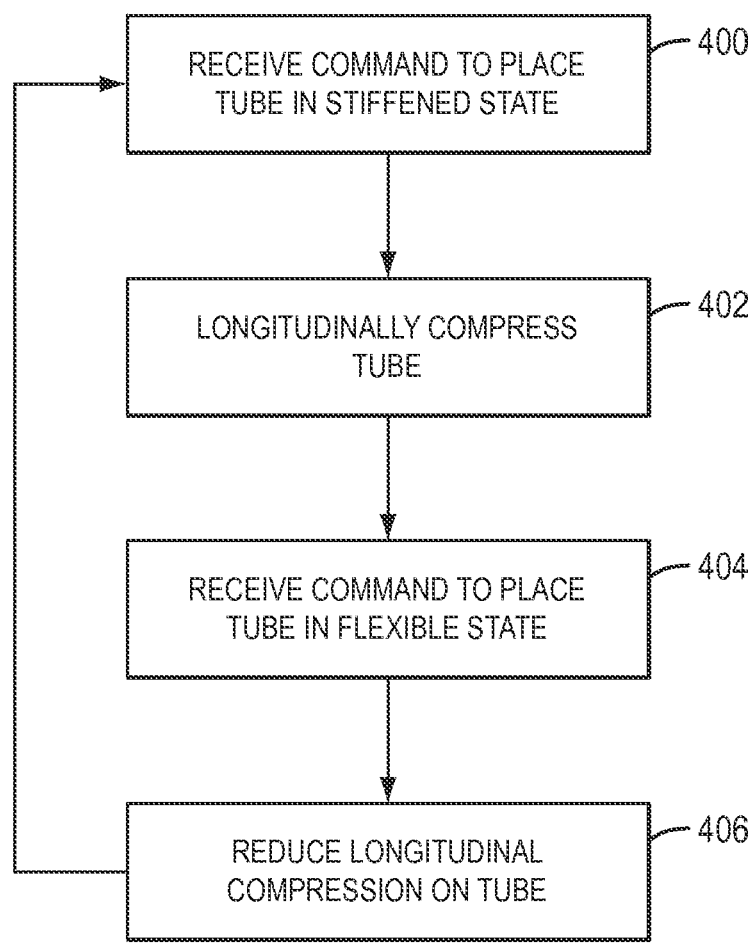
FIG. 12 is a flow diagram of a method for altering a surgical device between stiffened and flexible states in accordance with an exemplary embodiment of the present teachings.

In various additional exemplary embodiments, the disclosure relates to methods for altering a surgical device comprising a slitted flexible tube between stiffened and flexible states as described herein. FIG. 12, for example, shows a logic flow diagram depicting an exemplary method for a surgical device having the basic structure of device 900 of FIG. 9. As shown at step 400 of FIG. 12, a command is received, for example, from a control system (e.g., 355, FIG. 6), to place a surgical instrument tube (e.g., tube 904) in a stiffened state. At step 402, the tube is longitudinally compressed. As discussed above with reference to FIGS. 5C and 5D, longitudinally compressing the tube causes opposing surfaces of slits (e.g., slits 921) in the tube to contact one another, thereby preventing or substantially minimizing bending of the tube.

As shown at step 404 of FIG. 12, a command is then received to place the tube in a flexible state, and the tube is relaxed (i.e., the longitudinal compression on the tube is reduced), as indicated by the last step, 406. As discussed above with reference to FIGS. 5A and 5B, reducing the longitudinal compression on the tube allows the opposing surfaces of the slits to separate from one another, thereby permitting the tube to bend. In the flexible state, for example, the tube may passively bend upon external forces acting thereon, such as, for example, when the surgical instrument tube encounters a wall of the lumen and/or may actively bend upon actuation of one or more force transmission elements associated with the tube.

In various embodiments, to alter the tube between the stiffened and flexible states, the method may further comprise transmitting an actuation input to one or more force transmission elements associated with the tube, as described herein. In various embodiments, transmitting an actuation input to a force transmission element may comprise transmitting the actuation input to a plurality of cables (e.g., cables 931, 931', 931'', 932, 932', and/or 932'') associated with the tube. As discussed above with reference to FIG. 6, for example, in various embodiments, the tube may be longitudinally compressed by actuating the cables to provide a base pretension force; and the tube may be relaxed (i.e., the longitudinal compression on the tube may be reduced) by backdriving the cables to overcome the base pretension force. In an exemplary embodiment, an actuation mechanism such as that shown in FIG. 6 may be used to actuate the one or more force transmission elements.

Figure 13:
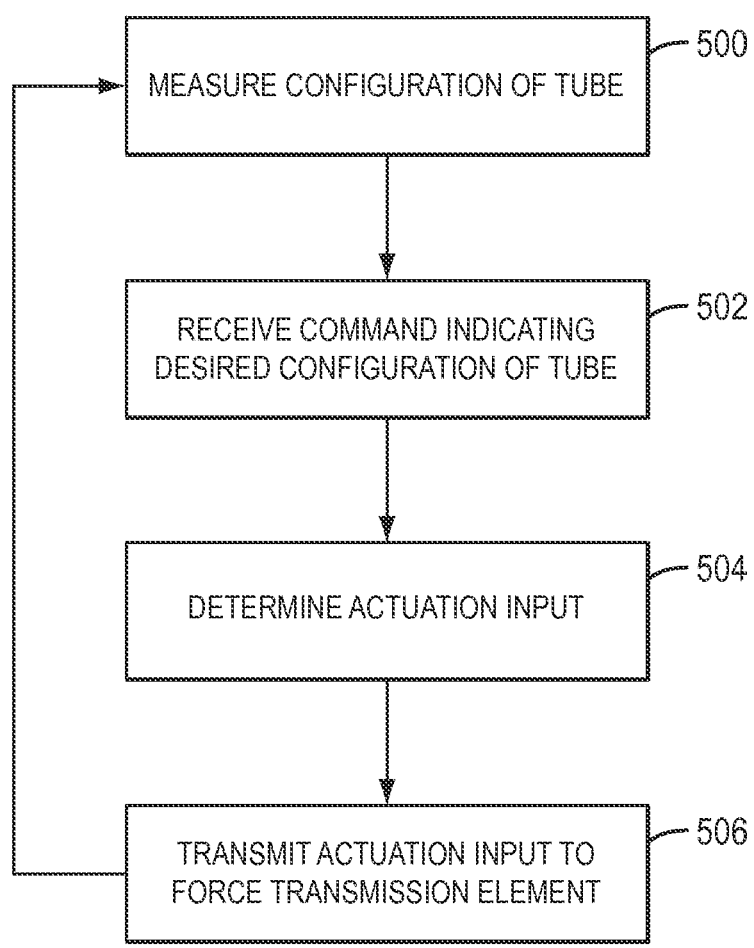
FIG. 13 is a flow diagram for actively controlling the configuration of the surgical device in accordance with the method of FIG. 12.

In various additional embodiments, as illustrated in FIG. 13, the method may further utilize shape sensing technology to actively control the bending of the tube. As shown, for example, at step 500 of FIG. 13, once a command to place the tube in a flexible state is received, the configuration of the tube can be measured, such as by measuring position and/or orientation of the tip (i.e., distal end) relative to the base (i.e., proximal end) of the tube. At step 502, a command that indicates the desired configuration of the tube (e.g., for a location at which a force transmission element is anchored) can be received, for example via a controller. At step 504, the controller can then determine an actuation input necessary to bend the tube from the measured configuration to the desired configuration, and that input can be transmitted to a force transmission element associated with the tube, as indicated by the last step, 506 of FIG. 13. As discussed above, a surgical device may implement various shape sensing technologies as disclosed, for example, in U.S. patent application Ser. No. 12/490,487 and U.S. Pat. No. 7,720,322 B2, the entire contents of which are incorporated by reference herein. It is, therefore, within the ability of one skilled in the art to select an appropriate method and control system for sensing and controlling the configuration of the tube, including for example, interrogating a sensor to generate position/orientation information about the tube and then, based on that information, controlling an actuator to control a force (e.g., tension or compression) on force transmission elements to thereby relax and/or stiffen the tube as desired in the manner explained above and as would be understood by those having ordinary skill in the art in light of the present teachings.

Although various exemplary embodiments shown and described herein relate to surgical devices comprising either passive, flexible tubes interconnected by joints, or active, continuously flexible tubes that can be used alone to replace a bendable serial link structure, those having ordinary skill in the art would understand that the slitted tubes described herein may have a broad range of application. In various embodiments, for example, as would be understood by those of ordinary skill in the art, tension elements may be attached to a flexible tube in a serial link structure such that tension on the tension elements may act directly on the tube (i.e., to actively bend the tube upon activation of one or more tension elements). In various additional embodiments, continuously flexible tubes (e.g., used to replace a serial link structure) can be modulated between active and passive states. As those of ordinary skill in the art would understand, for example, an actively flexible tube, when not actuated by its associated internally originating sources of force, may be passively flexible. Accordingly, in various embodiments, a surgical device may be configured (e.g., via a control system) to modulate between active and passive states by turning cable activation forces on and off.

Furthermore, although various exemplary embodiments shown and described herein relate to surgical devices used for minimally invasive procedures, those having ordinary skill in the art would understand that the structures and methods described may have a broad range of application to surgical devices, robotic and non-robotic, useful in a variety of applications for which both flexibility and rigidity are desired. Those having ordinary skill in the art would understand how to modify the exemplary embodiments described herein to provide surgical devices that can be varied between flexible and stiffened states for many types of surgical procedures.

The invention claimed is:

1. A method for operating a medical device comprising:
measuring a configuration of a tube;
receiving an indication of a desired configuration of the tube;
determining a first actuation input to bend the tube from the measured configuration to the desired configuration;
transmitting the first actuation input to at least one force transmission element coupled to the tube, the at least one force transmission element being actuatable to alter the tube between a flexible state and a stiffened state, wherein the at least one force transmission element comprises a first force transmission element and a second force transmission element and altering the tube from the flexible state to the stiffened state comprises simultaneously applying a first tension force to the first force transmission element and a second tension force to the second force transmission element to compress the tube and shorten a length of the tube;
receiving a first command to place the tube in the flexible state;
reducing longitudinal compression on the tube in response to the first command;
receiving a second command to place the tube in the stiffened state; and longitudinally compressing the tube in response to the second command.

2. The method of claim 1, wherein longitudinally compressing the tube comprises actuating the at least one force transmission element to provide a base pretension force.

3. The method of claim 1, wherein longitudinally compressing the tube comprises causing opposing surfaces of slits in the tube to move toward one another.

4. The method of claim 1, wherein the second tension force is equal to the first tension force.

5. The method of claim 1, wherein measuring the configuration of the tube comprises interrogating a sensor to measure at least one of a position or an orientation of at least a portion of the tube.

6. The method of claim 5, wherein the portion of the tube is a distal end of the tube.

7. The method of claim 6, wherein the at least one of the position or the orientation of the distal end of the tube is measured relative to a proximal end of the tube.

8. The method of claim 5, wherein the sensor is a fiber optic shape sensor.

9. A medical device comprising:
a tube;
at least one force transmission element coupled to the tube, the at least one force transmission element being actuatable to alter at least a portion of the tube between a flexible state and a stiffened state;
an actuator configured to apply actuation inputs to the at least one force transmission element, wherein the at least one force transmission element comprises a first force transmission element and a second force transmission element and altering the tube from the flexible state to the stiffened state comprises simultaneously applying with the actuator, a first tension force to the first force transmission element and a second tension force to the second force transmission element to compress the tube and shorten a length of the tube; and
a control system configured to:
measure a configuration of a tube;
receive an indication of a desired configuration of the tube;
determine a first actuation input to bend the tube from the measured configuration to the desired configuration;
transmit the first actuation input to the at least one force transmission element;
receive a first command to place the tube in the flexible state;
reduce longitudinal compression on the tube in response to the first command;
receive a second command to place the tube in the stiffened state; and
longitudinally compress the tube in response to the second command.

10. The medical device of claim 9, wherein longitudinally compressing the tube comprises actuating the at least one force transmission element to provide a base pretension force.

11. The medical device of claim 9, wherein longitudinally compressing the tube comprises causing opposing surfaces of slits in the tube to move toward one another.

12. The medical device of claim 9, wherein the second tension force is equal to the first tension force.

13. The medical device of claim 9, further comprising a sensor, wherein measuring the configuration of the tube comprises interrogating the sensor to measure at least one of a position or an orientation of at least a portion of the tube.

14. The medical device of claim 13, wherein the portion of the tube is a distal end of the tube.

15. The medical device of claim 14, wherein the at least one of the position or the orientation of the distal end of the tube is measured relative to a proximal end of the tube.

16. The medical device of claim 13, wherein the sensor is a fiber optic shape sensor.

* * * * *